(12) United States Patent
Kanazawa et al.

(10) Patent No.: US 12,352,753 B2
(45) Date of Patent: Jul. 8, 2025

(54) KIT FOR MEASURING MEASUREMENT TARGET SUBSTANCE AND METHOD FOR MEASURING MEASUREMENT TARGET SUBSTANCE

(71) Applicant: FUJIFILM Corporation, Tokyo (JP)

(72) Inventors: Yoshinori Kanazawa, Ashigarakami-gun (JP); Kazuhei Kaneko, Ashigarakami-gun (JP); Kouitsu Sasaki, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 764 days.

(21) Appl. No.: 17/393,578

(22) Filed: Aug. 4, 2021

(65) Prior Publication Data

US 2021/0364524 A1 Nov. 25, 2021

Related U.S. Application Data

(63) Continuation of application No. PCT/JP2020/004222, filed on Feb. 5, 2020.

(30) Foreign Application Priority Data

Feb. 6, 2019 (JP) ................. 2019-019586

(51) Int. Cl.
*G01N 33/58* (2006.01)
*G01N 21/64* (2006.01)

(52) U.S. Cl.
CPC ....... *G01N 33/582* (2013.01); *G01N 21/6428* (2013.01); *G01N 33/587* (2013.01); *G01N 2021/6439* (2013.01)

(58) Field of Classification Search
CPC . G01N 33/582; G01N 21/6428; G01N 33/587
See application file for complete search history.

(56) References Cited

U.S. PATENT DOCUMENTS

| 4,680,274 A | 7/1987 | Sakai et al. |
| 5,326,692 A | 7/1994 | Brinkley et al. |

(Continued)

FOREIGN PATENT DOCUMENTS

| CN | 1902490 A | 1/2007 |
| CN | 1944540 A | 4/2007 |

(Continued)

OTHER PUBLICATIONS

Chinese Office Action for Chinese Application No. 201880022538.9, dated Sep. 15, 2022, with English translation.

(Continued)

*Primary Examiner* — Lyle Alexander
*Assistant Examiner* — Dwan A Gerido
(74) *Attorney, Agent, or Firm* — Birch, Stewart, Kolasch & Birch, LLP

(57) ABSTRACT

An object of the present invention is to provide a kit for measuring a measurement target substance and a method for measuring a measurement target substance, which can exhibit a high noise suppression effect. According to the present invention, there is provide a kit for measuring a measurement target substance in a biological sample, which includes a luminescently labeled particle that has a first binding substance having a binding property to a measurement target substance, a substrate that has a detection area on a metal film having a second binding substance having a binding property to any one of the measurement target substance or the first binding substance, and a non-luminescent high molecular particle containing a predetermined structural unit.

6 Claims, 2 Drawing Sheets

(56) References Cited

U.S. PATENT DOCUMENTS

| | | |
|---|---|---|
| 5,433,896 A | 7/1995 | Kang et al. |
| 5,573,909 A | 11/1996 | Singer et al. |
| 5,670,381 A | 9/1997 | Jou et al. |
| 5,723,218 A | 3/1998 | Haugland et al. |
| 5,948,593 A | 9/1999 | Misawa et al. |
| 6,005,113 A | 12/1999 | Wu et al. |
| 10,816,469 B2 | 10/2020 | Kasagi et al. |
| 11,091,692 B2 | 8/2021 | Kanazawa et al. |
| 11,136,500 B2 | 10/2021 | Watanabe et al. |
| 11,519,860 B2 | 12/2022 | Chiku et al. |
| 11,674,954 B2 | 6/2023 | Chiku et al. |
| 11,733,244 B2 | 8/2023 | Chiku et al. |
| 11,821,896 B2 | 11/2023 | Chiku et al. |
| 2006/0172357 A1 | 8/2006 | Yang et al. |
| 2007/0154890 A1 | 7/2007 | Isobe |
| 2009/0261269 A1 | 10/2009 | Horii et al. |
| 2011/0054187 A1 | 3/2011 | Rurack et al. |
| 2013/0078738 A1 | 3/2013 | Watanabe et al. |
| 2014/0295468 A1 | 10/2014 | Kasagi et al. |
| 2015/0051101 A1 | 2/2015 | Hoshino et al. |
| 2015/0171328 A1 | 6/2015 | Bura et al. |
| 2016/0069909 A1 | 3/2016 | Nakamura et al. |
| 2016/0370289 A1 | 12/2016 | Hikage et al. |
| 2018/0372638 A1 | 12/2018 | Kasagi et al. |
| 2019/0185745 A1 | 6/2019 | Watanabe et al. |
| 2020/0018765 A1 | 1/2020 | Chiku et al. |
| 2020/0025748 A1 | 1/2020 | Chiku et al. |
| 2020/0025770 A1 | 1/2020 | Chiku et al. |
| 2020/0025771 A1* | 1/2020 | Chiku ................ C07D 209/56 |
| 2020/0033334 A1 | 1/2020 | Chiku et al. |
| 2020/0096445 A1 | 3/2020 | Chiku et al. |
| 2020/0378962 A1 | 12/2020 | Chiku et al. |
| 2021/0364524 A1 | 11/2021 | Kanazawa et al. |
| 2021/0380881 A1 | 12/2021 | Watanabe et al. |

FOREIGN PATENT DOCUMENTS

| | | | |
|---|---|---|---|
| CN | 102174144 A | | 9/2011 |
| CN | 103033492 A | | 4/2013 |
| CN | 105143234 A | | 12/2015 |
| CN | 105462576 A | | 4/2016 |
| CN | 106008581 A | | 10/2016 |
| EP | 2 966 080 A1 | | 1/2016 |
| EP | 2 995 952 A1 | | 3/2016 |
| JP | 60-256057 A | | 12/1985 |
| JP | 4-72564 A | | 3/1992 |
| JP | 7-508309 A | | 9/1995 |
| JP | 8-503547 A | | 4/1996 |
| JP | 10-153599 A | | 6/1998 |
| JP | 10-226172 A | | 8/1998 |
| JP | 10-508897 A | | 9/1998 |
| JP | 11-337551 A | | 12/1999 |
| JP | 2000-206115 A | | 7/2000 |
| JP | 2000-221196 A | | 8/2000 |
| JP | 2001-21563 A | | 1/2001 |
| JP | 3442777 B2 | | 9/2003 |
| JP | 2007-127438 A | | 5/2007 |
| JP | 2008-527332 A | | 7/2008 |
| JP | 2008-190946 A | | 8/2008 |
| JP | 2008190946 | * | 8/2008 |
| JP | 2008-249361 A | | 10/2008 |
| JP | 2010-19553 A | | 1/2010 |
| JP | 2010-112748 A | | 5/2010 |
| JP | 2010-190880 A | | 9/2010 |
| JP | 2012-47684 A | | 3/2012 |
| JP | 2012-199541 A | | 10/2012 |
| JP | 2014-196283 A | | 10/2014 |
| JP | 2014-235081 A | | 12/2014 |
| JP | 2015-72249 A | | 4/2015 |
| JP | 2016-57145 A | | 4/2018 |
| KR | 10-2014-0137676 A | | 12/2014 |
| WO | WO 92/21769 A1 | | 12/1992 |
| WO | WO 93/23492 A1 | | 11/1993 |
| WO | WO 96/29367 A1 | | 9/1996 |
| WO | WO 2013/146694 A1 | | 10/2013 |
| WO | WO 2014/013205 A1 | | 1/2014 |
| WO | WO 2015/129361 A1 | | 9/2015 |
| WO | WO 2017/150516 A1 | | 9/2017 |
| WO | WO 2018/021376 A1 | | 2/2018 |
| WO | WO 2018/021377 A1 | | 2/2018 |
| WO | WO 2018/038137 A1 | | 3/2018 |
| WO | WO 2018/038138 A1 | | 3/2018 |
| WO | WO 2018/181796 A1 | | 10/2018 |
| WO | WO 2018/181798 A1 | | 10/2018 |
| WO | WO 2018/181800 A1 | | 10/2018 |

OTHER PUBLICATIONS

Chinese Office Action for Chinese Application No. 201880022541.0, dated Aug. 26, 2022, with English translation.

European Communication pursuant to Article 94(3) EPC for corresponding European Application No. 19756950.2, dated Oct. 24, 2022.

U.S. Office Action for U.S. Appl. No. 16/585,231, dated Oct. 19, 2022.

U.S. Office Action for U.S. Appl. No. 16/585,306, dated Oct. 19, 2022.

U.S. Office Action for U.S. Appl. No. 16/585,758, dated Sep. 23, 2022.

Bartelmess et al., "Synthesis and Characterization of Far-Red/NIR-Fluorescent BODIPY Dyes, Solid-State Fluorescence, and Application as Fluorescent Tags Attached to Carbon Nano-onions," Chemistry—A European Journal, vol. 21, 2015, pp. 9727-9732, 6 pages total.

Brzeczek et al., "Systematic elongation of thienyl linkers and their effect on optical and electrochemical properties in carbazole-BODIPY donor-acceptor systems," RSC Advances, vol. 6, 2016, pp. 36500-36509, 10 pages total.

Chen et al., "Water-soluble, membrane-permeable organic fluorescent nanoparticles with large tunability in emission wavelengths and Stokes shifts," Chemistry Communications, vol. 49, 2013, pp. 5877-5879, 3 pages total.

Chinese Office Action and Search Report for Chinese Application No. 201780051809.9, dated May 31, 2021, with a partial English translation.

English translation of the International Preliminary Report on Patentability and Written Opinion of the International Searching Authority for International Application No. PCT/JP2018/013408, dated Oct. 1, 2019.

English translation of the International Preliminary Report on Patentability and Written Opinion of the International Searching Authority for International Application No. PCT/JP2018/013410, dated Oct. 1, 2019.

European Communication pursuant to Article 94(3) EPC for European Application No. 17843616.8, dated Nov. 19, 2020.

European Communication pursuant to Article 94(3) EPC for European Application No. 18774345.5, dated Feb. 15, 2021.

European Communication pursuant to Article 94(3) EPC for European Application No. 18774346.3, dated Feb. 15, 2021.

European Communication pursuant to Article 94(3) EPC for European Application No. 18775758.8, dated Feb. 16, 2021.

Extended European Search Report for European Application No. 17843616.8, dated Jun. 14, 2019.

Extended European Search Report for European Application No. 18774345.5, dated Feb. 10, 2020.

Extended European Search Report for European Application No. 18774346.3, dated Feb. 10, 2020.

Extended European Search Report for European Application No. 18775758.8, dated Feb. 10, 2020.

Extended European Search Report for European Application No. 19756950.2, dated Mar. 19, 2021.

Feng et al., "Regioselective and Stepwise Syntheses of Functionalized BODIPY Dyes through Palladium-Catalyzed Cross-Coupling Reactions and Direct C—H Arylations," The Journal of Organic Chemistry, vol. 81, 2016, pp. 6281-6291, 11 pages total.

Galangau et al., "Rational design of visible and NIR distyryl-BODIPY dyes from a novel fluorinated platform," Organic & Biomolecular Chemistry, vol. 8, 2010, pp. 4546-4553, 8 pages total.

(56) References Cited

OTHER PUBLICATIONS

Gómez-Durán et al., "Near-IR BODIPY Dyes à la Carte—Programmed Orthogonal Functionalization of Rationally Designed Building Blocks," Chemistry—A European Journal, vol. 22, 2016, pp. 1048-1061, 14 pages total.
Hecht et al., "Fluorinated Boron-Dipyrromethene (BODIPY) Dyes: Bright and Versatile Probes for Surface Analysis," ChemistryOpen, vol. 2, 2013, pp. 25-38, 14 pages total.
Hu et al., "Engineering Lysosome-Targeting BODIPY Nanoparticles for Photoacoustic Imaging and Photodynamic Therapy under Near-Infrared Light," ACS Applied Materials & Interfaces, vol. 8, 2016, pp. 12039-12047, 9 pages total.
International Preliminary Report on Patentability and Written Opinion of the International Searching Authority (Forms PCT/IB/373 and PCT/ISA/237) for International Application No. PCT/JP2017/030054 dated Feb. 26, 2019, with an English translation.
International Preliminary Report on Patentability and Written Opinion of the International Searching Authority (Forms PCT/IB/373 and PCT/ISA/237) for International Application No. PCT/JP2018/013406, dated Oct. 1, 2019, with an English translation.
International Preliminary Report on Patentability and Written Opinion of the International Searching Authority (Forms PCT/IB/373 and PCT/ISA/237) for International Application No. PCT/JP2019/006705, dated Aug. 27, 2020, with an English translation.
International Search Report (Form PCT/ISA/210) for International Application No. PCT/JP2017/030054, dated Oct. 10, 2017, with an English translation.
International Search Report (Form PCT/ISA/210) for International Application No. PCT/JP2018/013410, dated Jun. 26, 2018, with an English translation.
International Search Report and Written Opinion of the International Searching Authority (Forms PCT/ISA/210 and PCT/ISA/237) for International Application No. PCT/JP2019/006705, dated May 21, 2019, with an English translation.
Japanese Notice of Reasons for Refusal for Japanese Application No. 2018-524075, dated Feb. 4, 2020, with an English translation.
Japanese Notice of Reasons for Refusal for Japanese Application No. 2018-535725, dated Jan. 7, 2020, with an English translation.
Japanese Notice of Reasons for Refusal for Japanese Application No. 2019-510171, dated Jul. 21, 2020, with an English translation.
Japanese Notice of Reasons for Refusal for Japanese Application No. 2019-510173, dated Jul. 21, 2020, with an English translation.
Japanese Notice of Reasons for Refusal for Japanese Application No. 2019-510175, dated Jul. 21, 2020, with an English translation.
Japanese Notice of Reasons for Refusal for Japanese Application No. 2020-501053, dated Apr. 13, 2021, with an English translation.
Jiao et al., "Long wavelength red fluorescent dyes from 3,5-diiodo-BODIPYs," Organic & Biomolecular Chemistry, vol. 8, 2010, pp. 2517-2519, 3 pages total.
Korean Notification of Reason for Refusal for Korean Application No. 10-2019-7005239, dated Jan. 12, 2021, with an English translation.
Korean Notification of Reason for Refusal for Korean Application No. 10-2019-7005239, dated Jul. 15, 2020, with an English translation.
Korean Notification of Reason for Refusal for Korean Application No. 10-2019-7028398, dated Jan. 29, 2021, with an English translation.
Korean Notification of Reason for Refusal for Korean Application No. 10-2019-7028409, dated Jan. 14, 2021, with an English translation.
Küçüköz et al., "Enhancement of two photon absorption properties and intersystem crossing by charge transfer in pentaaryl boron-dipyrromethene (BODIPY) derivatives," Physical Chemistry Chemical Physics, vol. 18, 2016, pp. 13546-13553, 8 pages total.
Nagai et al., "Aromatic Ring-Fused BODIPY-Based Conjugated Polymers Exhibiting Narrow Near-Infrared Emission Bands," Macromolecules, vol. 43, 2010, pp. 193-200, 8 pages total.
Posthuma-Trumpie et al., "Development of a competitive lateral flow immunoassay for progesterone: influence of coating conjugates and buffer components," Analytical and Bioanalytical Chemistry, vol. 392, 2008, pp. 1215-1223, 9 pages total.
Rong et al., "Multicolor Fluorescent Semiconducting Polymer Dots with Narrow Emissions and High Brightness," ACS Nano, vol. 7, No. 1, 2013, pp. 376-384, 9 pages total.
Shi et al., "Tumor-targeting, enzyme-activated nanoparticles for simultaneous cancer diagnosis and photodynamic therapy," Journal of Materials Chemistry B, vol. 4, 2016, pp. 113-120, 8 pages total.
Sobenina et al., "Synthesis and Optical Properties of Difluorobora-s-diazaindacene Dyes with Trifluoromethyl meso-Substituents," European Journal of Organic Chemistry, 2013, pp. 4107-4118, 12 pages total.
Suda et al., "Multi-thiophene-substituted NIR boron-dibenzopyrromethene dyes: synthesis and their spectral properties," Tetrahedron, vol. 71, 2015, pp. 4174-4182, 9 pages total.
U.S. Office Action for U.S. Appl. No. 16/282,327, dated Feb. 8, 2021.
U.S. Office Action for U.S. Appl. No. 16/585,306, dated Jan. 18, 2022.
U.S. Office Action for U.S. Appl. No. 16/585,758, dated Dec. 7, 2021.
Wang et al., "Dihydronaphthalene-Fused Boron-Dipyrromethene (BODIPY) Dyes: Insight into the Electronic and Conformational Tuning Modes of BODIPY Fluorophores," Chemistry—A European Journal, vol. 16, 2010, pp. 2887-2903, 17 pages total.
Wild, "Logit-Log and Four-Parameter Log-Logistic Methods," The Immunoassay Handbook, Third Edition, 2005, pp. 238-240, 4 pages total.
Xu et al., "meso-C6F5 substituted BODIPYs with distinctive spectroscopic properties and their application for bioimaging in living cells," Tetrahedron, vol. 70, 2014, pp. 5800-5805, 6 pages total.
Zhao et al., "Stepwise Polychlorination of 8-Chloro-BODIPY and Regioselective Functionalization of 2,3,5,6,8-Pentachloro-BODIPY," The Journal of Organic Chemistry, vol. 80, 2015, pp. 8377-8383, 7 pages total.
Zhu et al., "Highly water-soluble neutral near-infrared emissive BODIPY polymeric dyes," Journal of Materials Chemistry, vol. 22, 2012, pp. 2781-2790, 10 pages total.
Chinese Office Action and Search Report for Chinese Application No. 201880022538.9, dated May 13, 2022, with an English translation.
Chinese Office Action and Search Report for Chinese Application No. 201880022541.0, dated May 11, 2022, with an English translation.
Chinese Office Action and Search Report for Chinese Application No. 201880022543.X, dated Apr. 25, 2022, with an English translation.
U.S. Office Action for U.S. Appl. No. 16/585,306, dated Jun. 6, 2022.
Chinese Office Action for Chinese Application No. 201780051809.9, dated Mar. 3, 2022, with English translation.
Extended European Search Report for corresponding European Application No. 20752374.7, dated Apr. 11, 2022.
Galangau et al., "Electrochromic and electrofluorochromic properties of a new boron dipyrromethene-ferrocene conjugate," Electrochimica Acta, vol. 87, 2013 (Available online Sep. 24, 2012), pp. 809-815.
Chinese Office Action for Chinese Application No. 201780051809.9, dated Jun. 13, 2022, with English translation.
Chinese Office Action for Chinese Application No. 201880022543.X, dated Aug. 5, 2022, with English translation.
Japanese Office Action for Japanese Application No. 2020-571226, dated Aug. 2, 2022, with English translation.
U.S. Office Action for U.S. Appl. No. 16/585,758, dated Apr. 22, 2022.
Chinese Office Action for Chinese Application No. 201980014801.4, dated Apr. 15, 2023, with an English translation.
U.S. Office Action for U.S. Appl. No. 16/999,138, dated Feb. 1, 2024.
Yamada et al., "Size Determination of Latex Particles by Electron Microscopy," Aerosol Science and Technology, vol. 4, 1985, pp. 227-232.

(56) References Cited

OTHER PUBLICATIONS

U.S. Office Action for U.S. Appl. No. 16/585,306, dated Mar. 6, 2023.
Chinese Office Action and Search Report for Chinese Application No. 201980014801.4, dated Dec. 16, 2022, with English translation.
Chinese Office Action for Chinese Application No. 201880022538.9, dated Jan. 9, 2023, with English translation.
Chinese Office Action for Chinese Application No. 201880022541.0, dated Jan. 5, 2023, with English translation.
Chinese Office Action for Chinese Application No. 201880022543.X, dated Jan. 9, 2023, with English translation.
Japanese Office Action for corresponding Japanese Application No. 2020-571226, dated Jan. 24, 2023, with English translation.
European Communication pursuant to Article 94(3) EPC for European Application No. 17843616.8, dated Jun. 12, 2023.
International Preliminary Report on Patentability (Form PCT/IPEA/409) for International Application No. PCT/JP2020/004222, dated Feb. 22, 2021, with an English translation.
International Search Report (Form PCT/ISA/210) for International Application No. PCT/JP2020/004222, dated Apr. 21, 2020, with an English translation.
"Theorie der Farbigkeit," Brands Chemie, Feb. 18, 2008, XP093129041, pp. 1-7, URL: <http://www.bhbrand.de/downloads/1farbigkeit.pdf>.
Chinese Office Action and Search Report for Chinese Application No. 201880022481.2, dated Jun. 1, 2022, with English translation.
Chinese Office Action and Search Report for Chinese Application No. 201880022530.2, dated Jul. 6, 2022, with English translation.
Chinese Office Action and Search Report for Chinese Application No. 201880022600.4, dated Jun. 13, 2022, with English translation.
European Communication pursuant to Article 94(3) EPC for corresponding European Application No. 17843616.8, dated Feb. 22, 2024.
European Office Action for European Application No. 18774205.1, dated Feb. 16, 2021.
European Office Action for European Application No. 18774876.9, dated Feb. 15, 2021.
European Office Action for European Application No. 18777743.8, dated Feb. 16, 2021.
Extended European Search Report for corresponding European Application No. 23204869.4, dated Mar. 7, 2024.
Extended European Search Report for European Application No. 18774205.1, dated Feb. 10, 2020.
Extended European Search Report for European Application No. 18774876.9, dated Feb. 10, 2020.
Extended European Search Report for European Application No. 18777743.8, dated Feb. 12, 2020.
Grazon et al., "Ultrabright BODIPY-Tagged Polystyrene Nanoparticles: Study of Concentration Effect on Photophysical Properties," The Journal of Physical Chemistry, vol. 118, Jun. 4, 2014, pp. 13495-13952.
International Preliminary Report on Patentability and English translation of the Written Opinion of the International Searching Authority (Forms PCT/IB/373 and PCT/ISA/237) for International Application No. PCT/JP2018/013405, dated Oct. 1, 2019.
International Preliminary Report on Patentability and English translation of the Written Opinion of the International Searching Authority (Forms PCT/IB/373 and PCT/ISA/237) for International Application No. PCT/JP2018/013407, dated Oct. 1, 2019.
International Preliminary Report on Patentability and English translation of the Written Opinion of the International Searching Authority (Forms PCT/IB/373 and PCT/ISA/237) for International Application No. PCT/JP2018/013409, dated Oct. 1, 2019.
International Search Report and Written Opinion of the International Searching Authority (Forms PCT/ISA/210 and PCT/ISA/237) for International Application No. PCT/JP2018/013405, dated Jun. 26, 2018, with English translation.
International Search Report and Written Opinion of the International Searching Authority (Forms PCT/ISA/210 and PCT/ISA/237) for International Application No. PCT/JP2018/013407, dated Jul. 3, 2018, with English translation.
International Search Report and Written Opinion of the International Searching Authority (Forms PCT/ISA/210 and PCT/ISA/237) for International Application No. PCT/JP2018/013409, dated Jul. 3, 2018, with English translation.
Japanese Office Action for Japanese Application No. 2019-510170, dated Jul. 21, 2020, with English translation.
Japanese Office Action for Japanese Application No. 2019-510172, dated Jul. 21, 2020, with English translation.
Japanese Office Action for Japanese Application No. 2019-510174, dated Jul. 21, 2020, with English translation.
Korean Office Action for Korean Application No. 10-2019-7028399, dated Jan. 2, 2021, with English translation.
Korean Office Action for Korean Application No. 10-2019-7028408, dated Jan. 14, 2021, with English translation.
Suda et al., "Multi-thiophene-substituted NIR boron-dibenzopyrromethene dyes: synthesis and their spectral properties," Tetrahedron, vol. 71, 2015, pp. 4174-4182.
U.S. Notice of Allowance for U.S. Appl. No. 16/583,870, dated Jun. 2, 2022.
U.S. Notice of Allowance for U.S. Appl. No. 16/585,406, dated Aug. 24, 2022.
U.S. Notice of Allowance for U.S. Appl. No. 16/585,406, dated Mar. 17, 2022.
U.S. Office Action for U.S. Appl. No. 16/583,870, dated Feb. 8, 2022.
U.S. Office Action for U.S. Appl. No. 16/583,870, dated Sep. 23, 2021.
U.S. Office Action for U.S. Appl. No. 16/584,079, dated Apr. 22, 2022.
U.S. Office Action for U.S. Appl. No. 16/584,079, dated Sep. 19, 2022.
U.S. Office Action for U.S. Appl. No. 16/585,406, dated Oct. 14, 2021.
Wang et al., "Synthesis, structure and photophysical properties of near-infrared 3,5-diarylbenzoBODIPY fluorophores," RSC Advances, vol. 6, 2016, pp. 52180-52188.
Yamaguchi et al., "How the π Conjugation Length Affects the Fluorescence Emission Efficiency," J. Am. Chem. Soc., vol. 130, 2008, pp. 13867-13869.
U.S. Office Action for U.S. Appl. No. 16/999,138, dated Jun. 20, 2024.
European Communication pursuant to Article 94(3) EPC for corresponding European Application No. 20752374.7, dated Sep. 3, 2024.
U.S. Notice of Allowance for U.S. Appl. No. 16/999,138, dated Dec. 24, 2024.
U.S. Appl. No. 16/282,327, filed Feb. 22, 2019.
U.S. Appl. No. 17/407,146, filed Aug. 19, 2021.
U.S. Appl. No. 16/585,306, filed Sep. 27, 2019.
U.S. Appl. No. 16/585,231, filed Sep. 27, 2019.
U.S. Appl. No. 16/585,758, filed Sep. 27, 2019.
U.S. Appl. No. 16/999,138, filed Aug. 21, 2020.
European Communication pursuant to Article 94(3) EPC for European Application No. 17843616.8, dated Mar. 19, 2025.

* cited by examiner

KIT FOR MEASURING MEASUREMENT TARGET SUBSTANCE AND METHOD FOR MEASURING MEASUREMENT TARGET SUBSTANCE

CROSS-REFERENCE TO RELATED APPLICATIONS

This application is a Continuation of PCT International Application No. PCT/JP2020/004222 filed on Feb. 5, 2020, which claims priority under 35 U.S.C § 119(a) to Japanese Patent Application No. 2019-019586 filed on Feb. 6, 2019. Each of the above application(s) is hereby expressly incorporated by reference, in its entirety, into the present application.

BACKGROUND OF THE INVENTION

1. Field of the Invention

The present invention relates to a kit for measuring a measurement target substance and a method for measuring a measurement target substance.

2. Description of the Related Art

A fluorescence detection method is widely used as a highly sensitive and easy measurement method for quantifying a protein, an enzyme, an inorganic compound, or the like. The fluorescence detection method is a method for confirming the presence of a measurement target substance by detecting the fluorescence emitted in a case where excitation light of a specific wavelength is applied to a sample considered to contain a measurement target substance which is excited by the light of a specific wavelength to emit fluorescence. In a case where the measurement target substance is not a fluorophore, the presence of the measurement target substance can be checked, for example, by bringing a substance in the state of being labeled with fluorescent dye, which specifically binds to the measurement target substance, into contact with a sample, and then detecting the fluorescence emitted in a case where excitation light is applied in the same manner as described above.

In the fluorescence detection method as described above, there is known a method for utilizing the effect of electric field enhancement by plasmon resonance to improve sensitivity for detecting a measurement target substance present in a small amount. In this method, in order to generate plasmon resonance, a sensor chip having a metal layer in a predetermined area on a transparent support is prepared, and excitation light is incident from a surface side of the support opposite to a surface on which metal layer is formed, with respect to an interface between the support and the metal film, at a predetermined angle equal to or more than the total reflection angle. The surface plasmon is generated in the metal layer by the irradiation with the excitation light, and the signal/noise ratio (S/N ratio) is improved by fluorescence enhancement, which is induced by the electric field enhancement effect caused by the generation of the surface plasmon, and thus high-sensitive measurement can be achieved. The fluorescence detection method by surface plasmon excitation (hereinafter referred to as "SPF method") is about 10 times stronger in a signal enhancement degree than the fluorescence detection method by epi-excitation (also referred to as epi-fluorescence method), and thus high-sensitive measurement can be achieved.

On the other hand, WO2013/146694 discloses a method for detecting a specific biological substance, which is a method for detecting a specific biological substance, in which a fluorophore-containing nanoparticle having a biological substance recognition molecule which is bound on the surface of the particle and specifically recognizes a specific biological substance is used as a coloring agent and a nanoparticle that does not contain a fluorophore is used as blocking agent for preventing the fluorophore-containing nanoparticle from non-specifically adsorbing to a biological substance other than the specific biological substance. In the method of WO2013/146694, a nanoparticle that does not contain a fluorophore is used as a means for suppressing noise.

JP1998-153599A (JP-H10-153599A) discloses a protein non-specific adsorption inhibitor characterized by containing an oxyalkylene group-containing acrylic polymer obtained by polymerizing a monomer represented by a predetermined structure. The protein non-specific adsorption inhibitor described in JP1998-153599A (JP-H10-153599A) is used for preventing non-specific adsorption of proteins not involved in the antigen-antibody reaction and for measuring an immunologically active substance with high sensitivity and high accuracy. In JP1998-153599A (JP-H10-153599A), an oxyalkylene group-containing acrylic polymer is used as a means for suppressing noise.

JP2012-47684A discloses a method for measuring fluorescence, which is characterized by at least including measuring the fluorescence emitted from a fluorescent molecule (A) in a complex consisting of a ligand formed on the surface of a substrate, an analyte, and a fluorescently labeled body to which a fluorescent molecule (A) is linked in the presence of an aqueous solution of a cationic water-soluble polymer (B).

SUMMARY OF THE INVENTION

An object to be achieved by the present invention is to provide a kit for measuring a measurement target substance and a method for measuring a measurement target substance, which can exhibit a high noise suppression effect.

As a result of diligent studies to achieve the above object, the inventors of the present invention have found that in a case where a luminescently labeled particle that has a first binding substance having a binding property to a measurement target substance and a substrate that has a detection area on a metal film having a second binding substance having a binding property to any one of the measurement target substance or the first binding substance are used to measure a measurement target substance in the biological sample, a high noise suppression effect can be achieved by carrying out the measurement using a mixture of the biological sample, the luminescently labeled particle, and a non-luminescent high molecular particle that contains a structural unit represented by Formula (A) or Formula (B), which is defined in the present specification. The present invention has been completed based on these findings.

That is, according to the present invention, the following inventions are provided.

<1> A kit for measuring a measurement target substance in a biological sample, the kit comprising:

a luminescently labeled particle that has a first binding substance having a binding property to a measurement target substance;

a substrate that has a detection area on a metal film having a second binding substance having a binding property to any one of the measurement target substance or the first binding substance; and a non-luminescent high molecular particle that contains a structural unit represented by Formula (A) or Formula (B),

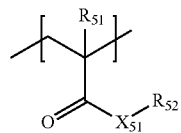

(A)

in the formula, $R_{51}$ represents a hydrogen atom or a methyl group, $X_{51}$ represents an oxygen atom or $NR_{53}$, and $R_{52}$ represents a hydrogen atom, a substituted or unsubstituted alkyl group, a substituted or unsubstituted aryl group, or a substituted or unsubstituted heteroaryl group, where $R_{53}$ represents a hydrogen atom, a substituted or unsubstituted alkyl group, a substituted or unsubstituted aryl group, or a substituted or unsubstituted heteroaryl group, and

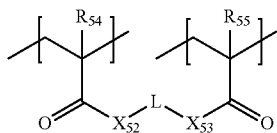

(B)

in the formula, $R_{54}$ and $R_{55}$ each independently represent a hydrogen atom or a methyl group, $X_{52}$ and $X_{53}$ each independently represent an oxygen atom or $NR_{56}$, and L represents a substituted or unsubstituted polyalkyleneoxy chain, a substituted or unsubstituted alkylene group, a substituted or unsubstituted arylene group, or a substituted or unsubstituted heteroarylene group, where $R_{56}$ represents a hydrogen atom, a substituted or unsubstituted alkyl group, a substituted or unsubstituted aryl group, or a substituted or unsubstituted heteroaryl group.

<2> The kit according to <1>, in which the non-luminescent high molecular particle contains a styrene unit, a divinylbenzene unit, a unit of acrylic acid or a salt thereof, or a unit of methacrylic acid or a salt thereof, as a structural unit other than the structural unit represented by Formula (A) or Formula (B).

<3> The kit according to <1> or <2>, in which the luminescently labeled particle is a particle that contains a fluorescent dye represented by Formula (1) or a fluorescent dye represented by Formula (10),

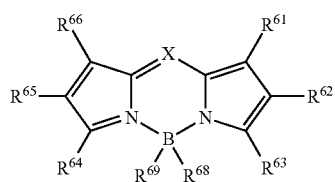

(1)

in the formula, X represents $CR^{67}$ or N, $R^{61}$ to $R^{67}$ represents a hydrogen atom, an alkyl group, a cycloalkyl group, an aliphatic heterocyclic group, an alkenyl group, a cycloalkenyl group, an alkynyl group, a hydroxyl group, a mercapto group, an alkoxy group, an alkylthio group, an aryloxy group, an arylthio group, an aryl group, a heteroaryl group, a halogen atom, a cyano group, a formyl group, an R—CO— group, a carboxy group, an R—O—CO— group, an R—CO—O— group, an $(R^4)_2N$—CO— group, an amino group, a nitro group, or a silyl group, which may further have a substituent, where R represents an alkyl group, a cycloalkyl group, an aliphatic heterocyclic group, an alkenyl group, a cycloalkenyl group, an alkynyl group, an aryl group, or a heteroaryl group, and $R^4$ represents a hydrogen atom, an alkyl group, a cycloalkyl group, an aliphatic heterocyclic group, an alkenyl group, a cycloalkenyl group, an alkynyl group, an aryl group, or a heteroaryl group, and $R^{68}$ and $R^{69}$ represent an alkyl group, a cycloalkyl group, an aliphatic heterocyclic group, an alkenyl group, a cycloalkenyl group, an alkynyl group, a hydroxyl group, a mercapto group, an alkoxy group, an alkylthio group, an aryloxy group, an arylthio group, an aryl group, a heteroaryl group, or a halogen atom, which may further have a substituent, and

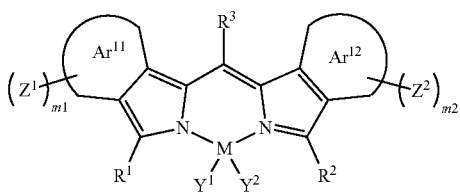

(10)

in the formula, m1 and m2 each independently represent an integer of 0 to 4, and any one of m1 or m2 is at least one, M represents a metalloid atom or a metal atom, $R^1$, $R^2$, and $R^3$ each independently represent a hydrogen atom, an alkyl group, an aryl group, a heterocyclic group, an ethenyl group, an ethynyl group, an acyl group, an alkoxy group, an aryloxy group, an alkylthio group, or an arylthio group, which may have a substituent, $Y^1$ and $Y^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, which may have a substituent, and $Y^1$ and $Y^2$ may be linked to each other to form a ring, $Ar^{11}$ and $Ar^{12}$ each independently represent an aromatic ring which may have a substituent, $Z^1$ and $Z^2$ each independently represent an aryl group, a heterocyclic group, or an amino group, which may have a substituent, and in a case where m1 is two or more, a plurality of $Z^1$'s may be the same group or groups different from each other, and in a case where m2 is two or more, a plurality of $Z^2$'s may be the same group or groups different from each other.

<4> The kit according to any one of <1> to <3>, in which the luminescently labeled particle have an average particle size of 50 to 300 nm.

<5> The kit according to any one of <1> to <4>, in which the non-luminescent high molecular particles have an average particle size of 10 to 300 nm.

<6> The kit according to any one of <1> to <5>, in which the polydispersion index of the non-luminescent high molecular particle is 0.40 or less.

<7> A method for measuring a measurement target substance in a biological sample, the method comprising:

a capturing step of bringing a mixture of a biological sample, a luminescently labeled particle that has a first binding substance having a binding property to a measurement target substance, and a non-luminescent high molecular particle that contains a structural unit represented by Formula (A) or Formula (B) into contact with a substrate that has a detection area on a metal film having a second binding substance having a binding property to any one of the measurement target substance or the first binding substance, thereby capturing the luminescently labeled particle on the substrate; and a label information acquisition step for acquiring label information related to the measurement target substance,

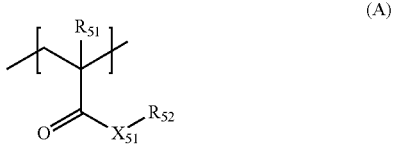

(A)

in the formula, $R_{51}$ represents a hydrogen atom or a methyl group, $X_{51}$ represents an oxygen atom or $NR_{53}$, and $R_{52}$ represents a hydrogen atom, a substituted or unsubstituted alkyl group, a substituted or unsubstituted aryl group, or a substituted or unsubstituted heteroaryl group, where $R_{53}$ represents a hydrogen atom, a substituted or unsubstituted alkyl group, a substituted or unsubstituted aryl group, or a substituted or unsubstituted heteroaryl group, and

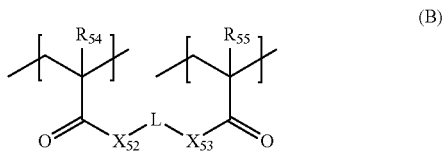

(B)

$R_{54}$ and $R_{55}$ each independently represent a hydrogen atom or a methyl group, $X_{52}$ and $X_{53}$ each independently represent an oxygen atom or $NR_{56}$, and L represents a substituted or unsubstituted polyalkyleneoxy chain, a substituted or unsubstituted alkylene group, a substituted or unsubstituted arylene group, or a substituted or unsubstituted heteroarylene group, where $R_{56}$ represents a hydrogen atom, a substituted or unsubstituted alkyl group, a substituted or unsubstituted aryl group, or a substituted or unsubstituted heteroaryl group.

<8> The method according to <7>, in which an amount of the non-luminescent high molecular particle used is 1 to 1,000 times an amount of the luminescently labeled particle used, in terms of a mass ratio.

According to the kit for measuring a measurement target substance according to the present invention, a high noise suppression effect can be achieved.

DESCRIPTION OF THE PREFERRED EMBODIMENTS

Figure 1:
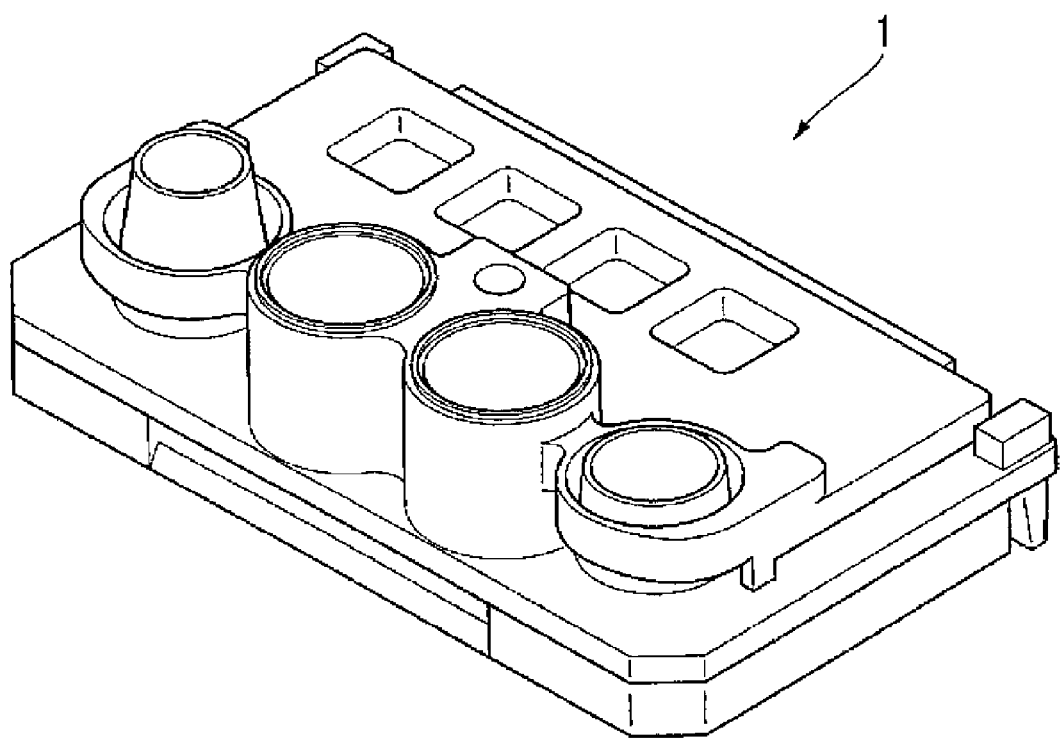
FIG. 1 is a schematic view illustrating a sensor chip.

Hereinafter, the embodiments of the present invention will be described in detail.

In the present specification, the numerical range indicated by using "to" means a range including numerical values described before and after "to" as a minimum value and a maximum value, respectively.

[Explanation of Terms]

The alkyl group may be any one of a linear alkyl group, a branched alkyl group, a cyclic alkyl group, or a combination thereof, and the number of carbon atoms in the linear or branched alkyl group is preferably 1 to 36, more preferably 1 to 18, still more preferably 1 to 12, and particularly preferably 1 to 6. Examples of the cyclic alkyl group include a cycloalkyl group having 3 to 8 carbon atoms. Specific examples of the alkyl group include a methyl group, an ethyl group, an n-propyl group, an isopropyl group, an n-butyl group, an iso-butyl group, a sec-butyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, and a cyclohexyl group.

Examples of the alkylene group include a group obtained by removing one hydrogen atom from the above-described alkyl group.

Examples of the polyalkyleneoxy chain include a group consisting of repeats of a group obtained by linking an alkylene group to an O atom. The alkylene group forming the polyalkyleneoxy chain is preferably an alkylene group having 2 to 4 carbon atoms, and an unsubstituted ethylene group, an ethylene group substituted with a methyl group, or an unsubstituted propylene group is particularly preferable.

The aliphatic heterocyclic group is not particularly limited, and examples thereof include groups derived from a 2-oxopyrrolidine ring, a piperidine ring, a piperazine ring, a morpholine ring, a tetrahydrofuran ring, a tetrahydropyran ring, a tetrahydrothiophene ring, and the like.

The alkenyl group may be any one of a linear alkyl group or a branched alkyl group, and the number of carbon atoms in the linear or branched alkyl group is preferably 2 to 36, more preferably 2 to 18, still more preferably 2 to 12, and particularly preferably 2 to 6. Examples of the alkenyl group include a vinyl group, an allyl group, a prenyl group, a geranil group, an oleyl group. Examples of the cycloalkenyl group include a cycloalkenyl group having 3 to 8 carbon atoms. Examples of the cycloalkenyl group include a 2-cyclopenten-1-yl group and a 2-cyclohexen-1-yl group.

The alkynyl group may be any one of a linear alkyl group or a branched alkyl group, and the number of carbon atoms in the linear or branched alkyl group is preferably 2 to 36, more preferably 2 to 18, still more preferably 2 to 12, and particularly preferably 2 to 6. Examples of the alkynyl group include an ethynyl group and a propargyl group.

The aryl group is preferably an aryl group having 6 to 48 carbon atoms, more preferably an aryl group having 6 to 24 carbon atoms, and still more preferably an aryl group having 6 to 14 carbon atoms, and examples thereof include a phenyl group, a naphthyl group, an anthryl group, a pyrenyl group, a phenanthrenyl group, a biphenyl group, and a fluorenyl group.

Examples of the arylene group include a group obtained by removing one hydrogen atom from the above-described aryl group.

In the present specification, the heterocyclic group is preferably any one of 5- to 7-membered heterocyclic groups which are substituted or unsubstituted, saturated or unsaturated, aromatic or non-aromatic, or monocyclic or fused. The heterocyclic group is preferably a heterocyclic group having a ring-constituting atom selected from a carbon atom, a nitrogen atom, an oxygen atom, and a sulfur atom, and having at least one hetero atom selected from a nitrogen atom, an oxygen atom, or a sulfur atom, and more preferably a 5- or 6-membered aromatic heterocyclic group having 3 to 30 carbon atoms. Examples of the heterocyclic group include a furyl group, a benzofuryl group, a dibenzofuryl group, a thienyl group, a benzothienyl group, a dibenzothienyl group, a pyridyl group, a pyrimidinyl group, a quinolyl group, an isoquinolyl group, an acridinyl group, a phenanthridinyl group, a pteridinyl group, a pyrazinyl group, a quinoxalinyl group, a pyrimidinyl group, a quinazolyl group, a pyridazinyl group, a cinnolinyl group, a phthalazinyl group, a triazinyl group, an oxazolyl group, a benzoxazolyl group, a thiazolyl group, a benzothiazolyl group, an imidazolyl group, a benzimidazolyl group, a pyrazolyl group, an indazolyl group, an isoxazolyl group, a benzisoxazolyl group, an isothiazolyl group, a benzisothiazolyl group, an oxadiazolyl group, a thiadiazolyl group, a triazolyl group, a tetrazolyl group, a furyl group, a thienyl group, a pyrrolyl group, an indolyl group, an imidazopyridinyl group, and a carbazolyl group.

In the present specification, the heteroaryl group is preferably any one of 5- to 7-membered heterocyclic groups which are substituted or unsubstituted, saturated or unsaturated, or monocyclic or fused. The heteroaryl group is preferably a heteroaryl group having a ring-constituting atom selected from a carbon atom, a nitrogen atom, an oxygen atom, and a sulfur atom, and having at least one hetero atom selected from a nitrogen atom, an oxygen atom, or a sulfur atom, and more preferably a 5- or 6-membered heteroaryl group having 3 to 30 carbon atoms. Examples of the heteroaryl group include an imidazolyl group, a pyridyl group, a quinolyl group, a furyl group, a thienyl group, a benzoxazolyl group, an indolyl group, a benzimidazolyl group, a benzthiazolyl group, a carbazolyl group, and an azepinyl group.

Examples of the heteroarylene group include a group obtained by removing one hydrogen atom from the above-described heteroaryl group.

In the present specification, the acyl group is preferably a linear or branched alkanoyl group having 2 to 15 carbon atoms, and examples thereof include an acetyl group, a propionyl group, a butyryl group, an isobutyryl group, a valeryl group, an isovaleryl group, a pivaloyl group, a hexanoyl group, a heptanoyl group, and a benzoyl group.

The alkoxy group is preferably an alkoxy group having 1 to 20 carbon atoms, and examples thereof include a methoxy group, an ethoxy group, a propoxy group, an n-butoxy group, a pentyloxy group, a hexyloxy group, and a heptyloxy group.

The aryloxy group is preferably an aryloxy group having 6 to 14 carbon atoms, and examples thereof include a phenoxy group, a naphthoxy group, and an anthryloxy group.

The alkylthio group is preferably an alkylthio group having 1 to 30 carbon atoms, and examples thereof include a methylthio group, an ethylthio group, and an n-hexadecylthio group.

The arylthio group is preferably an arylthio group having 6 to 30 carbon atoms, and examples thereof include a phenylthio group, a p-chlorophenylthio group, and an m-methoxyphenylthio group.

Examples of the halogen atom include a fluorine atom, a chlorine atom, a bromine atom, and an iodine atom.

Examples of the aromatic ring include aromatic hydrocarbon rings such as a benzene ring, a naphthalene ring, an anthracene ring, a phenanthrene ring, a pyrene ring, a perylene ring, and a terylene ring; aromatic heterocyclic rings such as an indene ring, an azulene ring, a pyridine ring, a pyrazine ring, a pyrimidine ring, a pyrazole ring, a pyrazolidine ring, a thiazolidine ring, an oxazolidine ring, a pyran ring, a chromene ring, a pyrrole ring, a pyrrolidine ring, a benzimidazole ring, an imidazoline ring, an imidazolidine ring, an imidazole ring, a pyrazole ring, a triazole ring, a triazine ring, a diazole ring, an indoline ring, a thiophene ring, a thienothiophene ring, a furan ring, an oxazole ring, an oxadiazole ring, a thiazine ring, a thiazole ring, an indole ring, a benzothiazole ring, a benzothiadiazole ring, a naphthothiazole ring, a benzoxazole ring, a naphthoxazole ring, an indolenine ring, a benzindolenine ring, a pyrazine ring, a quinoline ring, and a quinazoline ring; and fused aromatic rings such as a fluorene ring and a carbazole ring. An aromatic ring having 5 to 16 carbon atoms (an aromatic ring and a fused ring containing an aromatic ring) is preferable.

In addition, the aromatic ring may have a substituent, and the term "aromatic ring" means both an aromatic ring having a substituent and an aromatic ring having no substituent. Examples of the substituent of the aromatic ring include the substituents described in Substituent group A described later.

Examples of the amino group include an amino group; an alkyl-substituted amino group such as a mono- or dimethylamino group, a mono- or diethylamino group, or a mono or di(n-propyl)amino group; an amino group substituted with an aromatic residue such as a mono- or diphenylamino group or a mono- or a dinaphthylamino group; an amino group substituted with one alkyl group and one aromatic residue, such as a monoalkylmonophenylamino group; a benzylamino group, an acetylamino group, and a phenylacetylamino group. Here, the aromatic residue means a group in which one hydrogen atom is removed from an aromatic ring, and the aromatic ring is as described above in the present specification.

In the present specification, the "substituted or unsubstituted group" means that the corresponding group has a substituent or has no substituent. Regarding each of the groups in the present invention, it is described that a group may have a substituent in a case where the group may have a substituent. Examples of the substituent include the substituents described in Substituent group A. The substituent of Substituent group A may be further substituted with a substituent of Substituent group A.

Substituent Group A:

a sulfamoyl group, a cyano group, an isocyano group, a thiocyanato group, an isothiocyanato group, a nitro group, a nitrosyl group, a halogen atom, a hydroxy group, an amino group, a mercapto group, an amide group, an alkoxy group, an aryloxy group, an alkylthio group, an arylthio group, a carbamoyl group, an acyl group, an aldehyde group, a carbonyl group, an aryl group, an alkyl group, an alkyl group substituted with a halogen atom, an ethenyl group, an ethynyl group, a silyl group, and a trialkylsilyl group (such as a trimethylsilyl group).

[Kit for Measuring Measurement Target Substance in Biological Sample]

A kit for measuring a measurement target substance in a biological sample according to the present invention includes:

a luminescently labeled particle that has a first binding substance having a binding property to a measurement target substance;

a substrate that has a detection area on a metal film having a second binding substance having a binding property to any one of the measurement target substance or the first binding substance; and a non-luminescent high molecular particle that contains a structural unit represented by Formula (A) or Formula (B), which will be described later.

According to the present invention, a high noise suppression effect can be achieved, and at the same time, high sensitivity can be achieved. In the present invention, the signal/noise (S/N) ratio can be improved by using a non-luminescent high molecular particle that contains a structural unit represented by Formula (A) or Formula (B). In a case where the structural unit represented by Formula (A) or Formula (B) is present on the surface of the non-luminescent high molecular particle, it is presumed that the non-luminescent high molecular particle adsorbs noise-causing substances, whereby the selectivity in the antigen-antibody reaction of interest is improved. In a case where the non-luminescent high molecular particle is used, it is presumed that the structural unit represented by Formula (A) or Formula (B) is localized on the particle surface and adsorbs the noise-causing substances more efficiently.

(Non-Luminescent High Molecular Particle)

The non-luminescent high molecular particle that is used in the present invention include a structural unit represented by Formula (A) or Formula (B).

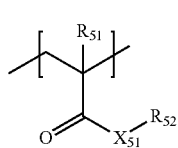

(A)

In the formula, $R_{51}$ represents a hydrogen atom or a methyl group. $X_{51}$ represents an oxygen atom or $NR_{53}$. $R_{52}$ represents a hydrogen atom, a substituted or unsubstituted alkyl group, a substituted or unsubstituted aryl group, or a substituted or unsubstituted heteroaryl group. Here, $R_{53}$ represents a hydrogen atom, a substituted or unsubstituted alkyl group, a substituted or unsubstituted aryl group, or a substituted or unsubstituted heteroaryl group.

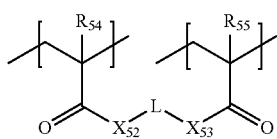

(B)

In the formula, $R_{54}$ and $R_{55}$ each independently represent a hydrogen atom or a methyl group. $X_{52}$ and $X_{53}$ each independently represent an oxygen atom or $NR_{56}$. L represents a substituted or unsubstituted polyalkyleneoxy chain, a substituted or unsubstituted alkylene group, a substituted or unsubstituted arylene group, or a substituted or unsubstituted heteroarylene group. Here $R_{56}$ represents a hydrogen atom, a substituted or unsubstituted alkyl group, a substituted or unsubstituted aryl group, or a substituted or unsubstituted heteroaryl group.

Examples of the non-luminescent high molecular particle include a high molecular particle such as a polystyrene bead and a glass particle such as a glass bead. Specific examples of the material of the particle include a synthetic polymer such as a polymer obtained by using a monomer such as styrene, methacrylic acid, glycidyl (meth)acrylate, butadiene, vinyl chloride, vinyl acetate acrylate, methyl methacrylate, ethyl methacrylate, phenyl methacrylate, or butyl methacrylate, or a copolymer obtained by using two or more monomers. The particle is preferably latex obtained by homogeneously suspending this synthetic polymer. In addition, other examples thereof include another organic polymer powder or inorganic substance powder, a microorganism, a blood cell, a cell membrane fragment, and a liposome. As described above, the non-luminescent high molecular particle may be a particle that contains a styrene unit, a divinylbenzene unit, a unit of acrylic acid or a salt thereof, or a unit of methacrylic acid or a salt thereof, as a structural unit other than the structural unit represented by Formula (A) or Formula (B).

In a case where latex particles are used, specific examples of the material of the latex include polystyrene, a styrene-acrylic acid copolymer, a styrene-methacrylic acid copolymer, a styrene-glycidyl (meth)acrylate copolymer, a styrene-styrene sulfonate copolymer, a methacrylic acid polymer, an acrylic acid polymer, an acrylonitrile-butadiene-styrene copolymer, a vinyl chloride-acrylic acid ester copolymer, and a vinyl acetate-(meth)acrylic acid ester copolymer. The latex is preferably a copolymer containing at least styrene as a monomer and particularly preferably a copolymer of styrene and acrylic acid or methacrylic acid. The method for preparing the latex is not particularly limited, and the latex can be prepared by any polymerization method.

In the non-luminescent high molecular particle, the structural unit represented by Formula (A) or Formula (B) is present on the surface of the solid phase. The method of introducing the structural unit represented by Formula (A) or Formula (B) is not particularly limited. For example, a particle having a copolymer containing the structural unit represented by Formula (A) or Formula (B), where the copolymer is present on the surface of the particle, can be produced by firstly preparing a core particle using such a method described above and then adding a monomer compound corresponding to the structural unit represented by Formula (A) or Formula (B) and, as desired, another monomer compound to the core particle to polymerize these monomer compounds.

Alternatively, in a case where the monomer compound corresponding to the structural unit represented by Formula (A) or Formula (B) is allowed to be present together when the core particle is prepared by such a method described above, the particle having a copolymer containing the structural unit represented by Formula (A) or Formula (B), where the copolymer is present on the surface of the particle, can be produced by selecting appropriate reaction conditions.

The preferred range of the average particle size of the non-luminescent high molecular particles is 10 nm or more and 300 nm or less, the more preferred range is 10 nm or more and 150 nm or less, and the still more preferred range is 20 nm or more and 100 nm or less.

The preferred range of the polydispersion index of the non-luminescent high molecular particles is 0.40 or less, the more preferred range is 0.20 or less, and the still more preferred range is 0.10 or less.

The average particle size and the polydispersion index of the non-luminescent high molecular particles can be measured by diluting 4.0 μL of an aqueous dispersion liquid having a solid content of 5% by mass of the non-luminescent high molecular particle with 796 μL of phosphate buffered saline (PBS, manufactured by FUJIFILM Wako Pure Chemical Corporation) (PH 7.4) and using Zetasizer Nano ZS (manufactured by Malvern Panalytical Ltd.).

Specific examples of the structural unit represented by Formula (A) are shown below.

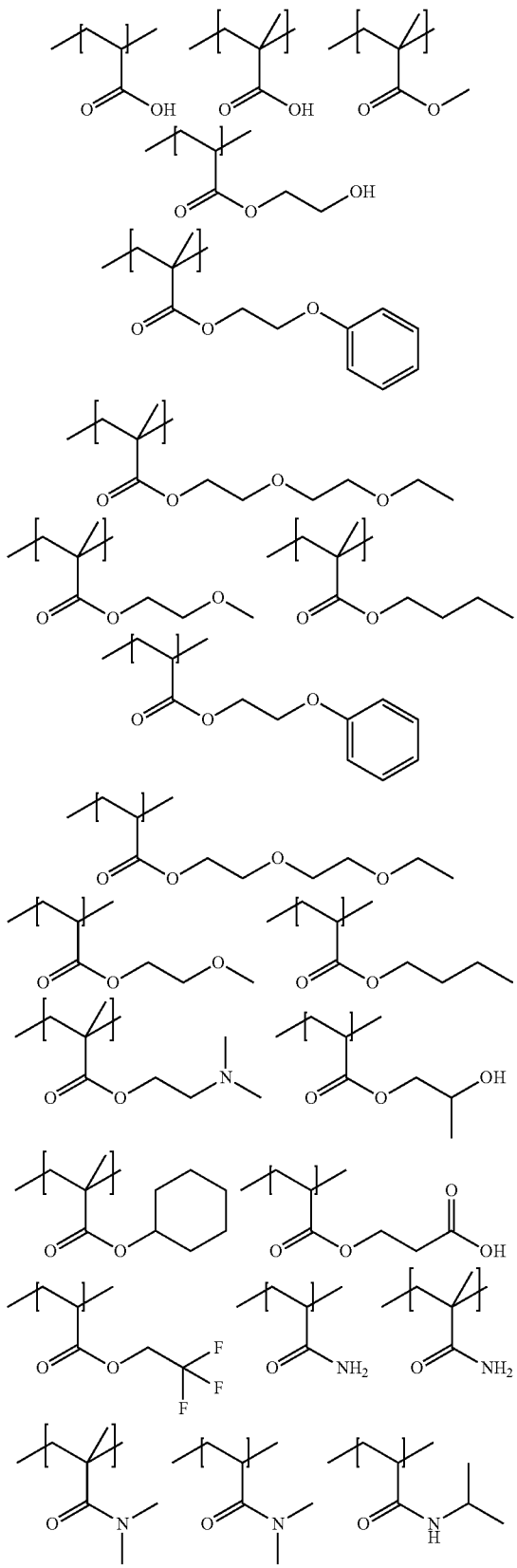

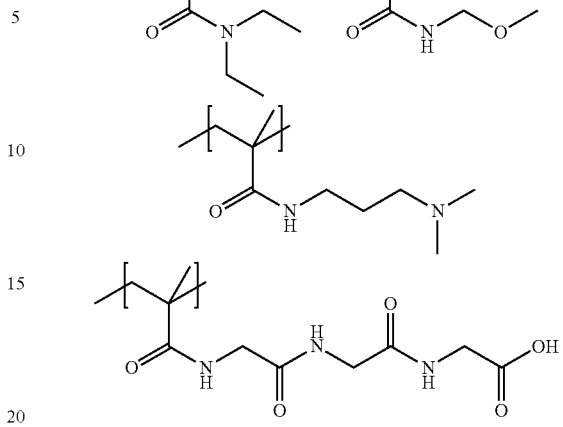

Specific examples of the structural unit represented by Formula (B) are shown below.

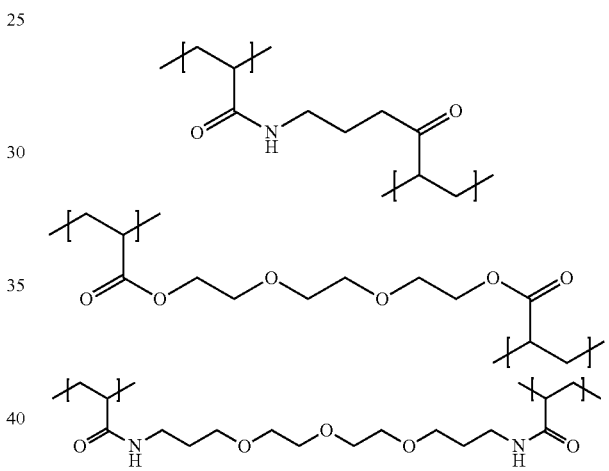

(Biological Sample)

The biological sample is not particularly limited as long as the sample is a sample that may contain the measurement target substance. For example, biologic samples, particularly body fluids (for example, blood, serums, plasma, spinal fluid, tears, sweat, urine, pus, runny nose, or sputum) or excrements (for example, feces), organs, tissues, mucous membranes, skin, or the like of animals (for example, humans, dogs, cats, horses, or the like) can be mentioned.

(Measurement Target Substance)

The measurement target substance is not particularly limited; however, examples thereof include thyroid stimulating hormone (TSH), thyroxine (T4), triiodothyronine (T3), estradiol (E2), aldosterone, symmetrical dimethyl arginine (SDMA), bile acid, cortisol, cholesterol, corticosterone, progesterone, testosterone, estrogen, vitamins, creatinine, amino acids, β-carotene, creatinine, digoxin, theophylline, folic acid, and a protein such as an inflammatory marker or a sepsis marker.

(First Binding Substance)

The first binding substance used in the present invention is a substance having a binding property to the measurement target substance. As the first binding substance, an antigen, an antibody, or a complex thereof can be used; however, the first binding substance is not limited thereto. Preferably, the first binding substance is an antibody. In a case where the first binding substance is an antibody, as antibodies having a binding property to the measurement target substance, for example, an antiserum prepared from a serum of an animal immunized with the measurement target substance, an immunoglobulin fraction purified from the antiserum, a monoclonal antibody obtained by cell fusion using spleen cells of an animal immunized with the measurement target substance, or a fragmented antibody [for example, F(ab')$_2$, Fab, Fab', or Fv] can be used. The preparation of these antibodies can be carried out by a conventional method. The fragmented antibody is a molecule obtained by an enzyme or chemical treatment or by using a genetic engineering technique. Further, the antibody may be modified as in the case of a chimeric antibody or the like, or a commercially available antibody or an antibody prepared from an animal serum or culture supernatant by known methods can be used.

In the present invention, an antibody can be used regardless of the animal species or the subclasses thereof. For example, an antibody that can be used in the present invention is an antibody derived from an organism in which an immune reaction can occur, such as mice, rats, hamsters, goats, rabbits, sheep, cows, or chickens, specific examples thereof include mouse IgG, mouse IgM, rat IgG, rat IgM, hamster IgG, hamster IgM, rabbit IgG, rabbit IgM, goat IgG, goat IgM, sheep IgG, sheep IgM, bovine IgG, bovine IgM, chicken IgY, and the like, and any one of polyclonal or monoclonal antibody can be used.

(Luminescently Labeled Particle)

The luminescently labeled particle that is used in the present invention is preferably a luminescently labeled particle that contains a luminescent compound and a particle and is also referred to as a fluorescently labeled particle.

The luminescently labeled particle is preferably a particle that contains a fluorescent dye represented by Formula (1) or a fluorescent dye represented by Formula (10) as the luminescent compound.

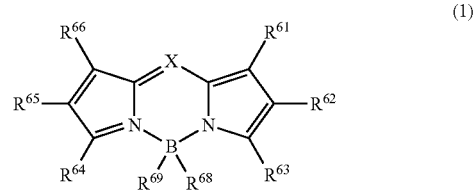
(1)

In the formula, X represents CR$^{67}$ or N.

R$^{61}$ to R$^{67}$ represents a hydrogen atom, an alkyl group, a cycloalkyl group, an aliphatic heterocyclic group, an alkenyl group, a cycloalkenyl group, an alkynyl group, a hydroxyl group, a mercapto group, an alkoxy group, an alkylthio group, an aryloxy group, an arylthio group, an aryl group, a heteroaryl group, a halogen atom, a cyano group, a formyl group, an R—CO— group, a carboxy group, an R—O—CO— group, an R—CO—O— group, an (R$^4$)$_2$N—CO— group, an amino group, a nitro group, or a silyl group, which may further have a substituent.

R represents an alkyl group, a cycloalkyl group, an aliphatic heterocyclic group, an alkenyl group, a cycloalkenyl group, an alkynyl group, an aryl group, or a heteroaryl group, and R$^4$ represents a hydrogen atom, an alkyl group, a cycloalkyl group, an aliphatic heterocyclic group, an alkenyl group, a cycloalkenyl group, an alkynyl group, an aryl group, or a heteroaryl group.

R$^{68}$ and R$^{69}$ represent an alkyl group, a cycloalkyl group, an aliphatic heterocyclic group, an alkenyl group, a cycloalkenyl group, an alkynyl group, a hydroxyl group, a mercapto group, an alkoxy group, an alkylthio group, an aryloxy group, an arylthio group, an aryl group, a heteroaryl group, or a halogen atom, which may further have a substituent.

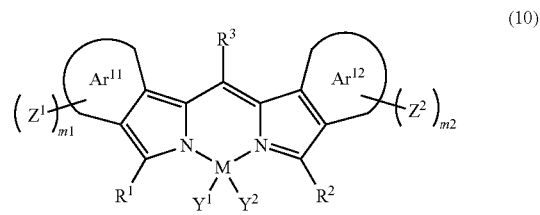
(10)

In the formula, m1 and m2 each independently represent an integer of 0 to 4, and any one of m1 or m2 is at least one, M represents a metalloid atom or a metal atom, R$^1$, R$^2$, and R$^3$ each independently represent a hydrogen atom, an alkyl group, an aryl group, a heterocyclic group, an ethenyl group, an ethynyl group, an acyl group, an alkoxy group, an aryloxy group, an alkylthio group, or an arylthio group, which may have a substituent, Y$^1$ and Y$^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, which may have a substituent, and Y$^1$ and Y$^2$ may be linked to each other to form a ring, Ar$^{11}$ and Ar$^{12}$ each independently represent an aromatic ring which may have a substituent, Z$^1$ and Z$^2$ each independently represent an aryl group, a heterocyclic group, or an amino group, which may have a substituent, and in a case where m1 is two or more, a plurality of Z$^1$'s may be the same group or groups different from each other, and in a case where m2 is two or more, a plurality of Z's may be the same group or groups different from each other.

As to Compound Represented by Formula (1A)

The fluorescent dye represented by Formula (1) may be a compound represented by Formula (1A).

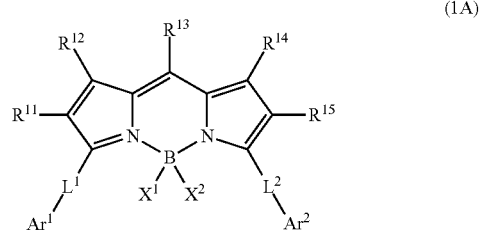
(1A)

In Formula (1A), R$^{11}$ to R$^{15}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, which may have a substituent. At least three of R$^{11}$, . . . , or R$^{15}$ represent an atom or a group other than the hydrogen atom, preferably at least four of R$^{11}$, . . . , or R$^{15}$ represent an atom or a group other than the hydrogen atom, and more preferably all of $R^{11}$ to $R^{15}$ represent an atom or a group other than the hydrogen atom.

$R^{11}$ and $R^{15}$ may be the same atom or group or atoms or groups different from each other; however, they are preferably the same atom or group. $R^{12}$ and $R^{14}$ may be the same atom or group or atoms or groups different from each other; however, they are preferably the same atom or group.

$R^{11}$ and $R^{15}$ preferably represent a hydrogen atom, a halogen atom, an alkyl group, an aryl group, a heterocyclic group, an ethenyl group, or an ethynyl group, which may have a substituent.

$R^{12}$ and $R^{14}$ preferably represent an alkyl group which may have a substituent.

$R^{13}$ preferably represents an aryl group which may have a substituent.

In Formula (1A), $X^1$ and $X^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, which may have a substituent, and $X^1$ and $X^2$ may be linked to each other to form a ring.

$X^1$ and $X^2$ preferably represent a halogen atom or an alkoxy group. $X^1$ and $X^2$ are more preferably a fluorine atom, a methoxy group, an ethoxy group, an isopropyloxy group, or a t-butyloxy group, which is also preferably substituted with a fluorine atom or an alkoxy group.

In Formula (1A), $Ar^1$ and $Ar^2$ each independently represent an aryl group or a heterocyclic group, which may have a substituent.

In Formula (1A), $L^1$ and $L^2$ each independently represent any one of Formula (L-1) to Formula (L-4).

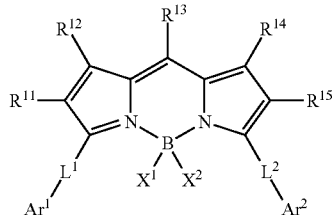

In the formula, $R^{11}$ to $R^{15}$, $X^1$, $X^2$, $Ar^1$, and $Ar^2$ are as defined in Formula (1A), and the preferred ranges thereof are also the same as the preferred ranges in Formula (1A). $L^{21}$ and $L^{22}$ each independently represent a group represented by Formula (L-1) or Formula (L-2).

As to Compound Represented by Formula (3)

Preferred examples of the compound represented by Formula (1) or Formula (1A) include a compound represented by Formula (3).

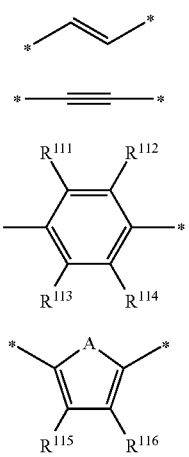

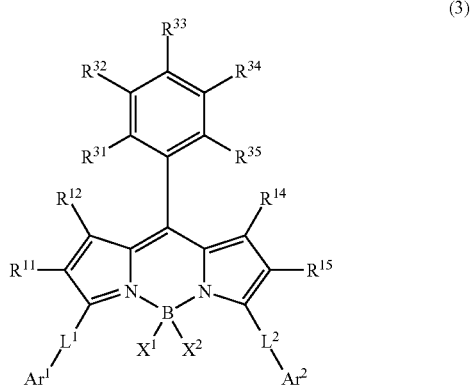

In the formulae, $R^{111}$ to $R^{116}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, which may have a substituent. A represents —O—, —S—, or —NH—.

L1 and L2 preferably represent any one of Formula (L-1) or Formula (L-2).

$R^{111}$ to $R^{116}$ are preferably a hydrogen atom.

As to Compound Represented by Formula (2)

Preferred examples of the compound represented by Formula (1) or Formula (1A) include a compound represented by Formula (2).

In Formula (3), $R^{11}$, $R^{12}$, $R^{14}$, $R^{15}$, $X^1$, $X^2$, $Ar^1$, $Ar^2$, $L^1$, and $L^2$ are as defined in Formula (1A), and preferred ranges thereof are also the same as the preferred ranges in Formula (1A). Here, at least two of $R^{11}$, $R^{12}$, $R^{14}$, or $R^{15}$ are an atom or a group other than the hydrogen atom, preferably at least three of $R^{11}$, $R^{12}$, $R^{14}$, or $R^{15}$ are an atom or a group other than the hydrogen atom, and more preferably $R^{11}$, $R^{12}$, $R^{14}$, and $R^{15}$ are an atom or a group other than the hydrogen atom.

In Formula (3), $R^{31}$ to $R^{35}$ each independently represent a hydrogen atom, a halogen atom, an alkyl group, an aryl group, a heterocyclic group, an ethenyl group, an ethynyl group, an amino group, a cyano group, an acyl group, an alkoxy group, an aryloxy group, an alkylthio group, or an arylthio group, which may have a substituent (examples of the substituent include the substituents described in Substituent group A), and any one of $R^{31}$, $R^{32}$, $R^{34}$, or $R^{35}$ is a group consisting of two or more atoms. The group consisting of two or more atoms is preferably an alkyl group, an aryl group, an ethenyl group, an ethynyl group, an amino group, a cyano group, or an alkoxy group and more preferably an alkyl group. Among the alkyl groups, an alkyl group consisting only of carbon atoms and hydrogen atoms or an alkyl group substituted with a halogen atom is preferable; an alkyl group consisting only of 1 to 6 carbon atoms and hydrogen atoms or an alkyl group substituted with a fluorine atom is more preferable; a methyl group, an isopropyl group, a t-butyl group, or a trifluoromethyl group is still more preferable; and a methyl group is particularly preferable.

As to Compound Represented by Formula (4)

Preferred examples of the compound represented by Formula (1) or Formula (1A) include a compound represented by Formula (4).

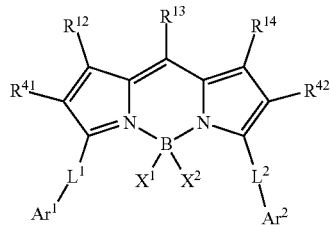

(4)

In Formula (4), $R^{12}$, $R^{13}$, $R^{14}$, $X^1$, $X^2$, $Ar^1$, $Ar^2$, $L^1$, and $L^2$ are as defined in Formula (1), and the preferred ranges thereof are also the same as the preferred ranges in Formula (1). Here, at least two of $R^{12}$, $R^{13}$, or $R^{14}$ are an atom or a group other than the hydrogen atom, preferably at least three of $R^{12}$, $R^{13}$, or $R^{14}$ are an atom or a group other than the hydrogen atom, and more preferably $R^{12}$, $R^{13}$, and $R^{14}$ are an atom or a group other than the hydrogen atom.

In Formula (4), $R^{41}$ and $R^{42}$ each independently represent an aryl group, a heterocyclic group, an ethenyl group, or an ethynyl group, which may have a substituent. Examples of the substituent include the substituents described in Substituent group A. $R^{41}$ and $R^{42}$ are each independently preferably an aryl group, an ethenyl group, or an ethynyl group, from the viewpoint of improving a quantum yield, an aryl group is preferable, and from the viewpoint of increasing a wavelength, an ethenyl group or an ethynyl group is preferable. In a case of an aryl group, it is preferable to have at least one substituent at the ortho or meta position of the aryl group, and it is more preferable to have at least one substituent at the ortho position of the aryl group. The number of the substituent substituted in the aryl group is preferably 1 to 3 and more preferably 2 or 3. The substituent substituted in the aryl group is preferably an alkyl group, more preferably a methyl group, an isopropyl group, or a t-butyl group, and still more preferably a methyl group.

As to Compound Represented by Formula (5)

Preferred examples of the compound represented by Formula (1) or Formula (1A) include a compound represented by Formula (5).

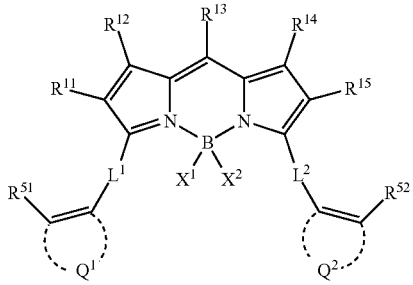

(5)

In Formula (5), $R^{11}$ to $R^{15}$, $X^1$, $X^2$, $L^1$, and $L^2$ are as defined in Formula (1A), and the preferred ranges thereof are also the same as the preferred ranges in Formula (1A).

In Formula (5), $R^{51}$ and $R^{52}$ each independently represent an alkyl group, an aryl group, a heteroaryl group, an amino group, an acyl group, an alkoxy group, an aryloxy group, an alkylthio group, or an arylthio group, which may have a substituent. Examples of the substituent include the substituents described in Substituent group A. $R^{51}$ and $R^{52}$ each independently are preferably an alkyl group or an alkoxy group, and from the viewpoint of improving a quantum yield, more preferably an alkyl group, still more preferably a methyl group, an ethyl group, an isopropyl group, or a t-butyl group, and particularly preferably a methyl group. From the viewpoint of increasing a wavelength, $R^{51}$ and $R^{52}$ each independently are more preferably an alkoxy group, still more preferably a methoxy group, an ethoxy group, an isopropyloxy group, or a t-butyloxy group, and particularly preferably a methoxy group.

$Q^1$ and $Q^2$ each independently represent an aromatic hydrocarbon ring or an aromatic heterocyclic ring, which may have a substituent. Examples of the substituent include the substituents described in Substituent group A. $Q^1$ and $Q^2$ are each preferably an aromatic hydrocarbon ring, more preferably a benzene ring, a naphthalene ring, an anthracene ring, a phenanthrene ring, or a pyrene ring, still more preferably a benzene ring or a naphthalene ring, and particularly preferably a benzene ring. As the group containing $R^{51}$ and forming $Q^1$ and the group containing $R^{52}$ and forming $Q^2$, a tolyl group, a xylyl group, or a mesityl group is preferable; a xylyl group or a mesityl group is more preferable; a xylyl group having methyl groups at both ends of the ortho position relative to the bonding position with $L^1$ or $L^2$, or a mesityl group having methyl groups at both ends of the ortho position and at the para position relative to the bonding position with $L^1$ or $L^2$ is still more preferable; and a mesityl group having methyl groups at both ends of the ortho position and at the para position relative to the bonding position with $L^1$ or $L^2$ is particularly preferable.

As to Compound Represented by Formula (6)

The compound represented by Formula (5) is more preferably a compound represented by Formula (6).

(6)

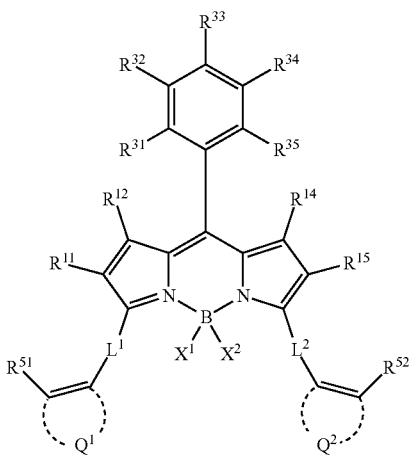

In the formula, $R^{11}$, $R^{12}$, $R^{14}$, and $R^{15}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, which may have a substituent, and at least two of $R^{11}$, $R^{12}$, $R^{14}$, or $R^{15}$ are an atom or a group other than the hydrogen atom. $X^1$ and $X^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, which may have a substituent, and $X^1$ and $X^2$ may be linked to each other to form a ring. $R^{31}$ to $R^{35}$ each independently represent a hydrogen atom, a halogen atom, an alkyl group, an aryl group, a heterocyclic group, an ethenyl group, an ethynyl group, an amino group, an acyl group, a cyano group, an alkoxy group, an aryloxy group, an alkylthio group, or an arylthio group, which may have a substituent, and any one of $R^{31}$, . . . , or $R^{35}$ is a hydrogen atom. $R^{51}$ and $R^{52}$ each independently represent an alkyl group, an aryl group, a heteroaryl group, an amino group, an acyl group, an alkoxy group, an aryloxy group, an alkylthio group, or an arylthio group, which may have a substituent. $Q^1$ and $Q^2$ each independently represent an aromatic hydrocarbon ring or an aromatic heterocyclic ring, which may have a substituent.

$L^1$ and $L^2$ each independently represent any one of Formula (L-1) to Formula (L-4),

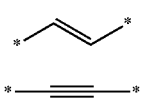 Formula (L-1)

 Formula (L-2)

Formula (L-3)

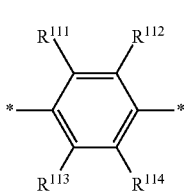

Formula (L-4)

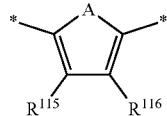

In the formulae, $R^{111}$ to $R^{116}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, which may have a substituent. A represents —O—, —S—, or —NH—.

$R^{11}$ and $R^{15}$ are each independently preferably an alkyl group, an aryl group, a heterocyclic group, an ethenyl group, an ethynyl group, or an amino group, more preferably that as defined in $R^{41}$ and $R^{42}$, that is, an aryl group, a heterocyclic group, an ethenyl group, or an ethynyl group, and still more preferably an aryl group, an ethenyl group, or an ethynyl group. From the viewpoint of improving a quantum yield, an aryl group is more preferable, and from the viewpoint of increasing a wavelength, an ethenyl group or an ethynyl group is more preferable. In a case of an aryl group, it is preferable to have at least one substituent at the ortho or meta position of the aryl group, and it is more preferable to have at least one substituent at the ortho position of the aryl group. The number of the substituent substituted in the aryl group is preferably 1 to 3 and more preferably 2 or 3. The substituent substituted in the aryl group is preferably an alkyl group, more preferably a methyl group, an isopropyl group, or a t-butyl group, and still more preferably a methyl group.

Specific Example of Compound Represented by Formula (1) to Formula (6)

Specific examples of the compound represented by Formula (1) to Formula (6) include the compounds described in paragraphs 0060 to 0065 of WO2018/181796.

Compound Represented by Formula (10)

(10)

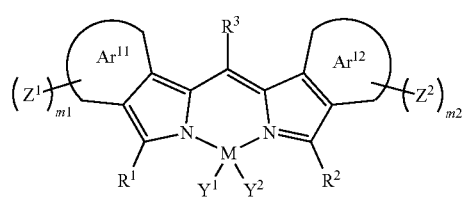

In Formula (10), m1 and m2 each independently represent an integer of 0 to 4, and any one of m1 or m2 is at least one. M represents a metalloid atom or a metal atom, $R^1$, $R^2$, and $R^3$ each independently represent a hydrogen atom, an alkyl group, an aryl group, a heterocyclic group, an ethenyl group, an ethynyl group, an acyl group, an alkoxy group, an aryloxy group, an alkylthio group, or an arylthio group, which may have a substituent, $Y^1$ and $Y^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, which may have a substituent, and $Y^1$ and $Y^2$ may be linked to each other to form a ring, $Ar^{11}$ and $Ar^{12}$ each independently represent an aromatic ring which may have a substituent, $Z^1$ and $Z^2$ each independently represent an aryl group, a heterocyclic group, or an amino group, which may have a substituent, and in a case where m1 is two or more, a plurality of $Z^1$'s may be the same group or groups different from each other, and in a case where m2 is two or more, a plurality of $Z^2$'s may be the same group or groups different from each other.

In Formula (10), m1 and m2 each independently represent an integer of 0 to 4, and preferably both m1 and m2 are one or more. m1 and m2 may be the same integer or integers different from each other and are preferably the same integer. Preferably, m1 and m2 are each independently one or two, more preferably, both m1 and m2 are one or two, and particularly preferably both m1 and m2 are one.

In Formula (10), M represents a metalloid atom or a metal atom, preferably a metalloid atom, and particularly preferably a boron atom.

In Formula (10), $R^1$, $R^2$, and $R^3$ each independently represent a hydrogen atom, an alkyl group, an aryl group, a heterocyclic group, an ethenyl group, an ethynyl group, an acyl group, an alkoxy group, an aryloxy group, an alkylthio group, or an arylthio group, which may have a substituent.

Preferably, $R^1$ and $R^2$ each independently represent an aryl group or a heterocyclic group, which may have a substituent.

$R^1$ and $R^2$ may be the same as or different from each other and are preferably the same as each other.

$R^1$ and $R^2$ are not linked to each other to form a ring.

Preferably, $R^3$ represents a hydrogen atom, an alkyl group, an aryl group, or a heterocyclic group, which may have a substituent. More preferably, $R^3$ is a hydrogen atom.

In Formula (10), $Y^1$ and $Y^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, which may have a substituent, and $Y^1$ and $Y^2$ may be linked to each other to form a ring.

Preferably, $Y^1$ and $Y^2$ each independently represent a halogen atom, an alkyl group, an aryl group, a hydroxy group, an alkoxy group, or an aryloxy group, which may have a substituent, and $Y^1$ and $Y^2$ may be linked to each other to form a ring.

More preferably, $Y^1$ and $Y^2$ are each independently a halogen atom.

Still more preferably, $Y^1$ and $Y^2$ are a fluorine atom.

$Y^1$ and $Y^2$ may be the same or different from each other and are preferably the same.

In Formula (10), $Ar^1$ and $Ar^2$ each independently represent an aromatic ring which may have a substituent.

Preferably, $Ar^1$ and $Ar^2$ each represent a benzene ring.

In Formula (10), Z1 to Z2 each independently represent a halogen atom, an alkyl group, an aryl group, a heterocyclic group, an ethenyl group, an ethynyl group, an acyl group, an alkoxy group, an aryloxy group, an alkylthio group, an arylthio group, or an amino group, which may have a substituent. In a case where m1 is two or more, a plurality of $Z^1$'s may be the same group or groups different from each other, and in a case where m2 is two or more, a plurality of $Z^2$'s may be the same group or groups different from each other.

Preferably, $Z^1$ and $Z^2$ each independently represent an aryl group which may have a substituent.

More preferably, $Z^1$ and $Z^2$ each independently represent a phenyl group, a naphthyl group, or an anthryl group, which may have a substituent.

Preferably, in a case where m1 is two or more, a plurality of $Z^1$'s are the same group.

Preferably, in a case where m2 is two or more, a plurality of $Z^2$'s are the same group.

It is preferable that the compound represented by Formula (2) does not have an acidic group such as a carboxylic acid group, a phosphoric acid group, or a sulfonic acid group, in the molecule.

As to Compound Represented by Formula (10A)

Preferred examples of the compound represented by Formula (10) include a compound represented by Formula (10A).

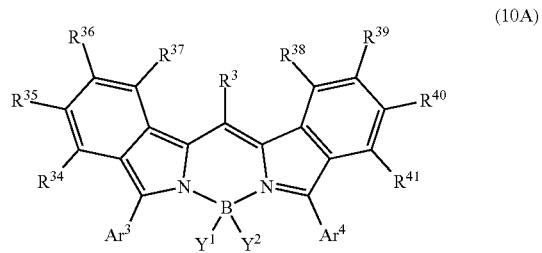

(10A)

In Formula (10A), $Y^1$ to $Y^2$ each independently represent a halogen atom, an alkyl group, an aryl group, a heterocyclic group, a hydroxy group, an alkoxy group, an aryloxy group, an alkylthio group, or an arylthio group, an ethenyl group, or an ethynyl group, which may have a substituent. Examples of the substituent include the substituents described in Substituent group A.

Preferably, $Y^1$ and $Y^2$ each independently represent a halogen atom.

Particularly preferably, $Y^1$ and $Y^2$ are a fluorine atom.

In Formula (10A), $R^3$ represents a hydrogen atom, an alkyl group, an aryl group, a heterocyclic group, an ethenyl group, an ethynyl group, or an acyl group, which may have a substituent.

Preferably, $R^3$ represents a hydrogen atom, an alkyl group, an aryl group, or a heterocyclic group, which may have a substituent.

More preferably, $R^3$ is a hydrogen atom.

In Formula (10A), $Ar^3$ and $Ar^4$ each independently represent an aryl group or a heterocyclic group, which may have a substituent. Examples of the substituent include the substituents described in Substituent group A.

In Formula (10A), $R^{34}$ to $R^{41}$ each independently represent a hydrogen atom, a halogen atom, an alkyl group, an aryl group, a heterocyclic group, an ethenyl group, an ethynyl group, an acyl group, an alkoxy group, an aryloxy group, an alkylthio group, an arylthio group, or an amino group, each of which may have a substituent. Examples of the substituent include the substituents described in Substituent group A.

In Formula (10A), at least one of $R^{34}$, . . . , or $R^{41}$ is preferably an aryl group which may have a substituent.

More preferably, at least one of $R^{34}$, . . . , or $R^{31}$ is an aryl group which may have a substituent, and at least one of $R^{38}$, . . . , or $R^{41}$ is an aryl group which may have a substituent.

More preferably, at least one of $R^{34}$, . . . , or $R^{41}$ is a group represented by Formula (11). Still more preferably, at least one of $R^{34}, \ldots,$ or $R^{37}$ is a group represented by Formula (11), and at least one of $R^{38}, \ldots,$ or $R^{41}$ is a group represented by Formula (11).

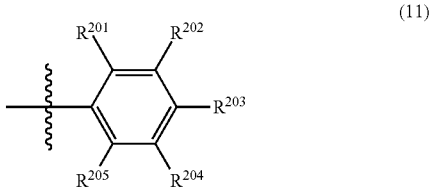
(11)

In Formula (11), $R^{201}$ to $R^{205}$ are each a hydrogen atom, a halogen atom, an alkyl group, an aryl group, a heterocyclic group, an ethenyl group, an ethynyl group, an acyl group, an alkoxy group, an aryloxy group, an alkylthio group, an arylthio group, or an amino group, and at least one of $R^{201}$ or $R^{205}$ is an atom or group other than a hydrogen atom. $R^{201}$ and $R^{202}$ may be linked to each other to form a ring, $R^{202}$ and $R^{203}$ may be linked to each other to form a ring, $R^{203}$ and $R^{204}$ may be linked to each other to form a ring, and $R^{204}$ and $R^{205}$ may be linked to each other to form a ring.

According to another preferred aspect, at least one of $R^{34}, \ldots,$ or $R^{41}$ is a group represented by Formula (12). Still more preferably, at least one of $R^{34}, \ldots,$ or $R^{37}$ is a group represented by Formula (12), and at least one of $R^{38}, \ldots,$ or $R^{41}$ is a group represented by Formula (12).

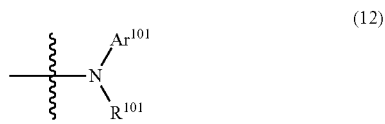
(12)

In Formula (12), $R^{101}$ represents a hydrogen atom, an alkyl group, an aryl group, a heterocyclic group, an ethenyl group, an ethynyl group, or an acyl group, which may have a substituent. Examples of the substituent include the substituents described in Substituent group A. $Ar^{101}$ represents an aryl group or a heterocyclic group, which may have a substituent. Examples of the substituent include the substituents described in Substituent group A. $Ar^{101}$ and $R^{101}$ may be linked to each other to form a ring.

It is preferable that the compound represented by Formula (10) does not have acidic groups, such as a carboxylic acid group, a phosphoric acid group, and a sulfonic acid group, in a molecule.

Specific Example of Compound Represented by Formula (10) or Formula (10A)

Specific examples of the compound represented by Formula (10) or Formula (10A) include the compounds described in paragraphs 0085 to 0092 of International Publication WO2018/181796.

<Amount of Luminescent Compound Used>

The content of the luminescent compound (for example, a fluorescent dye represented by Formula (1) or Formula (10) with respect to the particle before the addition of the luminescent compound is not particularly limited; however, the content thereof is preferably 0.5 μmol/g to 400 μmol/g, more preferably 1 μmol/g to 300 μmol/g, still more preferably 2 μmol/g to 200 μmol/g, and particularly preferably 3 μmol/g to 100 μmol/g.

The content of the luminescent compound with respect to the particle before the addition of the luminescent compound is not particularly limited; however, the content thereof is preferably 0.1% by mass to 30% by mass, more preferably 0.2% by mass to 20% by mass, still more preferably 0.3% by mass to 10% by mass, and particularly preferably 0.4% by mass to 8% by mass.

<Particle>

The luminescently labeled particle contains a particle. The material and the form of the particle are not particularly limited, and for example, organic high molecular particles such as a polystyrene bead and an inorganic particle such as a glass bead can be used. Specific examples of the material of the particle include a homopolymer obtained by polymerizing a monomer such as styrene, methacrylic acid, glycidyl (meth)acrylate, butadiene, vinyl chloride, vinyl acetate, methyl methacrylate, ethyl methacrylate, phenyl methacrylate, or butyl methacrylate, and a copolymer obtained by polymerizing two or more monomers. The particle may be latex obtained by homogeneously suspending the above homopolymer or copolymer. In addition, examples of the particle include another organic polymer powder or inorganic substance powder, a microorganism, a blood cell, a cell membrane fragment, a liposome, and a microcapsule. The particle is preferably a latex particle.

In a case where latex particles are used, specific examples of the material of the latex include polystyrene, a styrene-acrylic acid copolymer, a styrene-methacrylic acid copolymer, a styrene-glycidyl (meth)acrylate copolymer, a styrene-styrene sulfonate copolymer, a methacrylic acid polymer, an acrylic acid polymer, an acrylonitrile-butadiene-styrene copolymer, a vinyl chloride-acrylic acid ester copolymer, and a vinyl acetate-acrylic acid ester copolymer. The latex is preferably a copolymer containing at least styrene as a monomer and particularly preferably a copolymer of styrene and acrylic acid or methacrylic acid. The method for preparing the latex is not particularly limited, and the latex can be prepared by any polymerization method. However, in a case where the luminescent labeled particle is used by being labeled with an antibody, the presence of a surfactant makes it difficult to immobilize the antibody, and thus an emulsifier-free emulsion polymerization, that is, an emulsion polymerization without using an emulsifier such as a surfactant is preferable.

<Method for Measuring Average Particle Size (Average Particle Size) of Luminescently Labeled Particles>

The average particle size of the luminescently labeled particles varies depending on the material of the particle, the concentration range for measuring the test substance, the measuring device, and the like; however, it is preferably in a range of 0.001 to 10 μm (more preferably 0.01 to 1 μm), more preferably in a range of 30 to 500 nm, still more preferably in a range of 50 to 300 nm, particularly preferably in a range of 80 to 200 nm, and most preferably in a range of 100 to 150 nm. The preferred range of the polydispersion index of the luminescently labeled particles is 0.40 or less, the more preferred range is 0.20 or less, and the still more preferred range is 0.10 or less. The average particle size and the polydispersion index of the luminescently labeled particles can be measured with a commercially available particle size distribution meter or the like. As a method for measuring the average particle size distribution, optical microscopy, confocal laser microscopy, electron microscopy, atomic force microscopy, static light scattering method, laser diffraction method, dynamic light scattering method, centrifugal sedimentation method, electric pulse measurement method, chromatography method, ultrasonic attenuation method, and the like are known, and apparatuses corresponding to the respective principles are commercially available. Among these measurement methods, it is preferable to measure the average particle size and the polydispersion index of the luminescent labeled particles using a dynamic light scattering method from the viewpoint of the particle size range and ease of measurement. Examples of the commercially available measuring apparatus using dynamic light scattering include NANOTRAC UPA (Nikkiso Co., Ltd.), dynamic light-scattering particle size analyzer LB-550 (HORIBA, Ltd.), fiber-optics particle analyzer FPAR-1000 (Otsuka Electronics Co., Ltd.), and Zetasizer Nano ZS (manufactured by Malvern Panalytical, Ltd.). In the present invention, the average particle size is obtained as a median diameter (d=50) measured at 25° C. under the conditions of a viscosity of 0.8872 CP and a refractive index of water of 1.330.

<Method for Producing Luminescently Labeled Particle>

The method for producing a luminescently labeled particle is not particularly limited; however, the luminescently labeled particle can be produced by mixing a luminescent compound with a particle. For example, the luminescently labeled particle can be prepared by adding the luminescent compound represented by Formula (1) to a particle such as a latex particle. More specifically, the luminescent labeled particles can be produced by adding a solution containing the compound represented by Formula (1) to a dispersion liquid that contains at least one of water or a water-soluble organic solvent (tetrahydrofuran, methanol, or the like) and stirring the mixture.

In the present invention, a dispersion liquid containing the luminescently labeled particle may be prepared.

The dispersion liquid can be produced by dispersing the luminescently labeled particles in a dispersion medium. Examples of the dispersion medium include water, an organic solvent, and a mixture of water and an organic solvent. An alcohol such as methanol, ethanol, or isopropanol, an ether-based solvent such as tetrahydrofuran, or the like can be used as the organic solvent.

The concentration of the solid content of the luminescently labeled particle in the dispersion liquid is not particularly limited; however, it is generally 0.1% to 20% by mass, preferably 0.5% to 10% by mass, and more preferably 1% to 5% by mass.

(Modification of Luminescently Labeled Particle by First Binding Substance)

The method for immobilizing the first binding substance on the luminescent labeled particle is described, for example, in JP2000-206115A or the protocol attached to FluoSpheres (registered trade mark) polystyrene microsphere F8813 of Thermo Fisher Scientific Inc., and any known method for preparing a reagent for an immunoagglutination reaction can be used. In addition, as a principle of immobilizing an antibody as a binding substance on particles, any principle of physical adsorption or a chemical bond by a covalent bond can be adopted. As a blocking agent (that is, a first blocking agent) covering a particle surface that is not coated with the antibody after immobilizing the antibody on the particle, for example, albumin (such as BSA), skim milk, casein, a soybean-derived component, a fish-derived component, polyethylene glycol, or the like, and commercially available blocking agents for an immune reaction or the like containing the substances as well as substances having the same property as that of the substances can be used. These blocking agents can be subjected to a pretreatment such as partial modification with heat, acid, alkali, or the like, as necessary. Further, as the first blocking agent, an antibody (globulin) which has no binding property to the measurement target substance or a protein (Protein A and Protein G) which is not used in a test area can be used.

A specific method for immobilizing an antibody on particles is exemplified below. An antibody solution of which concentration is adjusted to 0.01 to 20 mg/mL is added to a liquid in which the particles are dispersed such that the concentration of the solid content of the particles becomes 0.1% to 10% by mass, and mixing is carried out. Stirring is continued for 5 minutes to 48 hours under a condition of a temperature of 4° C. to 50° C. Next, the particle and the solution are separated by centrifugation or other methods to sufficiently remove antibodies not bound to the particle contained in the solution. Then, an operation of washing the particle with a buffer solution is repeated 0 to 10 times. It is preferable that after carrying out an operation of mixing the particle with the antibody and binding the antibody to the particle, a portion of the particle surface to which the antibody is not bound is protected using a blocking agent such as a component which does not participate in the antigen-antibody reaction, preferably protein and more preferably globulin, albumin, BLOCKACE (registered trade mark), skim milk, or casein.

In a case where the antigen, the antibody, or the like is immobilized on the particle, a stabilizer can be added, as necessary. The stabilizer is not particularly limited as long as the stabilizer stabilizes an antigen or an antibody, like a synthetic polymer or a natural polymer, such as polysaccharides or sucrose, and commercially available stabilizers such as Immunoassay Stabilizer (Advanced Biotechnologies Inc.) can also be used.

The labeled particle having the first binding substance is contained in the kit according to the embodiment of the present invention, and an aspect in which the labeled particle is contained in a container, for example, a cup, which is a part of the kit is preferable. In this case, the measurement target substance in the biological sample can be bound to the first binding substance by injecting the biological sample into a container containing the labeled particle and mixing and stirring components.

(Substrate)

In the present invention, in order to achieve high-sensitive measurement, it is preferable to adopt a measurement method for carrying out surface plasmon fluorescence (SPF) detection described later. As a substrate in this case, it is preferable to use a substrate having a metal film on a surface. A metal constituting the metal film is not particularly limited as long as the metal can cause surface plasmon resonance. Preferably, free-electron metals such as gold, silver, copper, aluminum, or platinum can be mentioned, and gold is particularly preferable. In a case where gold is used, the detection area described later is on the gold film. The metals can be used singly or in a combination thereof. Further, in consideration of the adhesiveness to the substrate, an intervening layer including chromium or the like may be provided between the substrate and the layer including metal. The thickness of the metal film is randomly determined; however, for example, is preferably 1 nm or more and 500 nm or less, and particularly preferably 10 nm or more and 200 nm or less. In a case where the thickness exceeds 500 nm, a surface plasmon phenomenon of a medium cannot be detected sufficiently. In addition, in a case of providing an intervening layer which includes chromium or the like, it is preferable that the thickness of the intervening layer is 0.1 nm or more and 10 nm or less.

The formation of the metal film may be carried out by a conventional method and can be carried out, for example, by a sputtering method, a vapor deposition method, an ion plating method, an electroplating method, a non-electrolytic plating method, or the like. However, for providing a mixed layer of a substrate material and a metal film to improve the adhesiveness of the metal film, it is preferable to prepare the metal film by the sputtering method. In this case, the thickness of the mixed layer of the substrate material and the metal film is not particularly limited as long as sufficient adhesiveness can be ensured, and 10 nm or less is preferable.

The metal film is preferably disposed on the substrate. Here, "disposed on the substrate" includes a case where the metal film is disposed to be in direct contact with the substrate and a case where the metal film is disposed not in direct contact with the substrate but in contact with the substrate through other layers. The material of the substrate that can be used in the present invention is, for example, optical glass such as BK7 (borosilicate glass), which is a type of general optical glass, or synthetic resin, specifically a substance formed of a material transparent to laser light, such as polymethyl methacrylate, polyethylene terephthalate, polycarbonate, or a cycloolefin polymer can be used. Such a substrate is preferably a material that does not exhibit anisotropy with respect to polarization and has excellent processability.

As a preferred aspect of the substrate for SPF detection, a substrate in which a gold film is vapor-deposited on polymethyl methacrylate (PMMA) can be mentioned.

The substrate has a detection area having a second binding substance having a binding property to any one of the measurement target substance or the first binding substance.

(Second Binding Substance)

The second binding substance is a substance having a binding property to the measurement target substance, or a substance having a binding property to the first binding substance. In a case where the quantification is carried out by a sandwich assay method, a substance having a binding property to the measurement target substance can be used as the second binding substance. In a case where the quantification is carried out by a competition method, a substance having a binding property to the first binding substance can be used as the second binding substance.

The second binding substance is not particularly limited; however, examples thereof include an antigen, an antibody, or a complex thereof. The second binding substance is preferably an antigen, and it is particularly preferable to use a measurement target substance (this is a substance having a binding property to the first binding substance) as the second binding substance.

In a case where a measurement target substance is used as the second binding substance, the second binding substance is preferably a conjugate of the measurement target substance and a carrier. The carrier means a substance to which a plurality of molecules of the measurement target substance can be bound. Examples of the preferred carrier include proteins, and among them, specific examples thereof include bovine serum albumin.

In a case where the measurement target substance is TSH, the second binding substance is preferably an anti-TSH antibody.

(Method for Immobilizing Second Binding Substance on Substrate)

A method for immobilizing the second binding substance on the substrate is described in, for example, Tech Notes Vols. 2 to 12 provided by Nunc Corporation and all known methods for preparing a general enzyme-linked immunosorbent assay (ELISA) reagent can be used. In addition, surface modification may be carried out by placing a self-assembled monolayer (SAM) or the like on a substrate, and as the method for immobilizing the second binding substance on the substrate, any one of a method using physical adsorption or a method using chemical bonding by a covalent bond can be also adopted. As a blocking agent (a first blocking agent) covering the substrate surface which is not coated with the antibody, after immobilizing the second binding substance on the substrate, known substances such as BSA, globulin, skim milk, casein, a soybean-derived component, a fish-derived component, and polyethylene glycol, commercially available blocking agents for an immune reaction containing the above substances or substances having the same properties as those of the above substances, and the like can be used. These blocking agents can be subjected to a pretreatment such as partial modification with heat, acid, alkali, or the like, as necessary.

(Detection Area <Test Area>)

In the present invention, a test area can be provided on the substrate to detect the presence or absence of the measurement target substance in the biological sample. In this test area, for example, an antigen can be quantified by capturing an antigen which is a measurement target substance and detecting and quantifying the amount of labels bound to the antigen. Alternatively, the antigen can be quantified by a method in which only the labels bound to the antigen are allowed not to be bound and only labels not bound to the antigen are captured to calculate the amount of labels bound to the antigen. This detection method is referred to as the competition method and here, the substrate related to the competition method will be described.

It is preferable that the test area of the substrate has a site for reacting with the binding substance (for example, antibody) present on the labeled particle. As a preferred aspect of the present invention, an aspect in which the antigen present in the biological sample is on the test area of the substrate is preferable. In this case, the antigen and BSA are reacted in the presence of a condensing agent to prepare an antigen-BSA conjugate, and a test area can be prepared by adsorbing the conjugate onto the test area. The antigen-BSA conjugate which is the measurement target substance can be bound to the test area on a substrate by a method in which the conjugate is dissolved in a buffer solution, and the resultant is spotted on the substrate and left to stand for a predetermined time, the supernatant is aspirated, and drying is carried out.

(Reference Area <Control Area>)

In the present invention, in order to minimize the influence of the measurement environment, particularly the measurement temperature, as much as possible, a control area is provided on the substrate, and the information on the test area is standardized by the information on the control area, thereby enabling the environmental dependency to be suppressed extremely low. The control area is preferably designed to be capable of binding to all the labels regardless of the amount of the measurement target substance present in the biological sample to be used. It is preferable to provide an antibody that interacts with all the antibodies present on the labeled particle. By designing in this manner to standardize the information on the test area by the information on the control area, for example, even in a case where the flow of the biological sample or the reaction rate is affected in the low temperature environment, such influence can be canceled by the standardization, and thus it is possible to obtain a result that is always precise and not affected by the measurement environment.

An antibody to be present in the control area preferably has a function of recognizing a binding substance (for example, antibody) present on the labeled particle, in a case where the antibody is derived from a mouse, an anti-mouse antibody is preferable, and in a case where the antibody on the labeled particle is derived from a goat, an anti-goat antibody is preferable. These antibodies on the control area can be bound to a substrate by a method in which the antibodies are dissolved in a buffer solution, and the resultant is spotted on the substrate and left to stand for a predetermined time, the supernatant is aspirated, and drying is carried out.

(Blocking Agent)

For example, in the competition method, not only a negative biological sample which does not contain a measurement target substance but also a biological sample which becomes negative by reacting to even a positive biological sample which contains a measurement target substance are present, and the solution to the problem of deviation at a high value is recognized as an issue. The causes of the false negative are not clear; however, one of the causes is considered to be that labeled particles which are originally not desired to bind to the detection area but bind to the detection area are present due to non-specific interaction between the labeled particle surface not covered with the antibody and the detection area (the test area). In addition, in a case where the same substance as the substance present on the test area is present on the surface of the labeled particle, and a free antibody or the like is present in the biological sample, even in the measurement of a positive biological sample containing the measurement target substance, the antibody may be detected as negative by binding to both the substances present on the test area and the substance on the surface of the labeled particle.

In general, blocking with BSA is used to suppress non-specific adsorption onto a solid phase surface (for example, a labeled particle surface, and a gold film surface of a substrate).

As an immunoglobulin other than the immunoglobulin having a binding property to the measurement target substance, specifically, an antiserum prepared from a serum of an animal immunized with an antigen different from the measurement target substance, an immunoglobulin fraction purified from the antiserum, a monoclonal antibody obtained by cell fusion using spleen cells of an animal immunized with the measurement target substance, or a fragment thereof [for example, F(ab')$_2$, Fab, Fab', or Fv] can be used. The preparation of these antibodies can be carried out by a conventional method. Further, the antibody may be modified as in the case of a chimeric antibody or the like, or a commercially available antibody or an antibody prepared from an animal serum or culture supernatant by known methods can be used.

(Other Elements of Kit)

The kit according to the embodiment of the present invention is used for a method for measuring a measurement target substance, and in a case where the measurement target substance is TSH, it is a kit for TSH measurement diagnosis. In the present invention, in the case of carrying out measurement of a measurement target substance, the kit includes a substrate on which a second binding substance is immobilized and a sensor chip including a member holding labeled particles such as fluorescent particles; however, the kit may include various instruments or apparatuses used in the measurement of a measurement target substance, such as a surface plasmon excitation apparatus and a fluorescence measurement device. Further, a sample containing a known amount of the measurement target substance, an instruction manual, or the like may be included as an element of the kit.

[Method for Measuring Measurement Target Substance in Biological Sample]

The method for measuring a measurement target substance in a biological sample according to the present invention is a method that includes:

a capturing step of bringing a mixture of a biological sample, a luminescently labeled particle that has a first binding substance having a binding property to a measurement target substance, and a non-luminescent high molecular particle that contains a structural unit represented by Formula (A) or Formula (B) into contact with a substrate that has a detection area on a metal film having a second binding substance having a binding property to any one of the measurement target substance or the first binding substance, thereby capturing the luminescently labeled particle on the substrate; and a label information acquisition step for acquiring label information related to the measurement target substance.

In the present invention, the measurement target substance can be measured by the measurement target substance-related label information acquisition step of acquiring label information related to the amount of the measurement target substance.

In the present invention, the amount of the non-luminescent high molecular particle used is preferably 1 to 1,000 times, more preferably 1 to 100 times, still more preferably 1 to 50 times, and particularly preferably 1 to 30 times the amount of the luminescently labeled particle used, in terms of the mass ratio.

The measurement in the present invention is interpreted as the broadest concept as long as the measurement is a measurement of the amount of the measurement target substance. Specific examples of the embodiment of the measurement method include the competition method and the sandwich method.

As an example of the competition method, a case of quantifying progesterone will be described below. The same can also be applied to the case of quantifying substances other than progesterone.

In the competition method, first, a progesterone immunoassay substrate on which a progesterone-albumin conjugate is immobilized is brought into contact with a biological sample containing progesterone, an anti-progesterone antibody-labeled fluorescent particle, and a non-luminescent high molecular particle containing a structural unit represented by Formula (A) or Formula (B). In a case where progesterone is not present in the biological sample, an antigen-antibody reaction occurs on the substrate by the anti-progesterone antibody-labeled fluorescent particle and progesterone on the substrate (that is, progesterone in a progesterone-albumin conjugate). On the other hand, in a case where progesterone is present in the biological sample, an antigen-antibody reaction occurs between progesterone in the biological sample and the anti-progesterone antibody-labeled fluorescent particle, and an antigen-antibody reaction between the anti-progesterone antibody-labeled fluorescent particle and the progesterone on the substrate (that is, progesterone in the progesterone-albumin conjugate) is inhibited. After the above reaction is completed, anti-progesterone antibody-labeled fluorescent particles that do not bind to albumin on the substrate are removed. Then, by detecting a degree of formation of an immune complex (that is, the complex of the anti-progesterone antibody-labeled fluorescent particle and progesterone in the progesterone-albumin conjugate on the substrate) on the substrate as fluorescence intensity, the concentration of progesterone or the like in the biological sample can be measured.

The configuration of the fluorescence measurement in the competition method can adopt any one of plate reader measurement or flow measurement, and for example, the measurement can be carried out by the following method. A plurality of samples having known amounts of progesterone and having different progesterone concentrations are prepared in advance, and these samples and the anti-progesterone antibody-labeled fluorescent particles are mixed in advance. This mixed solution is brought into contact with an area where the progesterone-albumin conjugate is immobilized. The fluorescence signal from the area where the progesterone-albumin conjugate is immobilized is measured as a plurality of fluorescence signals while the mixed solution is in contact with the conjugate at specific time intervals. From the plurality of fluorescence signals, the temporal change (the slope) in the fluorescence amount is acquired at each progesterone concentration. The temporal change is plotted as a Y axis and the progesterone concentration is plotted as an X axis, and a relational expression of the progesterone concentration with respect to the temporal change in the fluorescence amount is acquired using an appropriate fitting method such as the least squares method. The amount of progesterone contained in the biological sample can be quantified using the result of the temporal change in the fluorescence amount using the biological sample to be tested based on the relational expression thus acquired.

It is preferable to carry out this quantification of the amount of progesterone in a short time. Specifically, the quantification is preferably carried out within 10 minutes, more preferably within 8 minutes, and still more preferably within 6 minutes. This quantification time preferably includes the time required to convert the amount of progesterone which is contained in the biological sample, based on the result of the temporal change in the fluorescence amount acquired using the biological sample to be tested after the sample and the anti-progesterone antibody-labeled fluorescent particles are brought into contact with detection area where the progesterone-albumin conjugate is immobilized, by using the relational expression between the temporal change in the fluorescence amount and the progesterone concentration, which is acquired in advance using an appropriate fitting method such as the least squares method.

The sandwich method is not particularly limited and for example, the measurement target substance can be measured by the following procedure. A biological sample which may contain a measurement target substance, fluorescent particles having a first binding substance having a binding property to the measurement target substance, and a non-luminescent high molecular particle that contains a structural unit represented by Formula (A) or Formula (B) are brought into contact with each other on a substrate. In a case where the measurement target substance is present in the biological sample, a binding reaction (such as an antigen-antibody reaction) occurs among the measurement target substance, the fluorescent particles, and the substrate. As a result, in a case where the measurement target substance is present in the biological sample, an immune complex including a second binding substance bound to the substrate, the measurement target substance, and the fluorescent particles having the first binding substance are formed. In the sandwich method, after a reaction among the second binding substance, the measurement target substance, and the fluorescent particles having the first binding substance is completed, fluorescent particles having a first binding substance, which do not form the above-described immune complex, are removed and washing is carried out. Next, the concentration of the measurement target substance or the like can be measured by detecting the degree of the formation of the immune complex as fluorescence intensity. The fluorescence intensity and the concentration of the measurement target substance have a positive correlation.

(Flow Channel)

In the preferred aspect of the present invention, a mixed solution obtained by mixing a biological sample that may contain a measurement target substance, a luminescently labeled particle that has a first binding substance, and a non-luminescent high molecular particle that contains a structural unit represented by Formula (A) or Formula (B) is applied onto a substrate and developed into a flow channel. The flow channel is not particularly limited as long as the flow channel is a passage that allows the biological sample, the luminescently labeled particle that has a first binding substance, and the non-luminescent high molecular particle to flow down to the detection area. The preferred aspect of the flow channel is a flow channel having a structure in which a spotting port for spotting a biological sample solution containing the luminescently labeled particle that has a first binding substance and the non-luminescent high molecular particle, a metal film as the detection area, and a flow channel beyond the metal film are provided and the biological sample can pass over the metal film. Preferably, an aspiration port can be provided on a side opposite to the spotting port with respect to the metal film.

(Surface Plasmon Fluorescence Measurement)

The method for detecting a label such as fluorescence in the present invention is not particularly limited. For example, it is preferable that fluorescence intensity is detected using a device capable of detecting fluorescence intensity, specifically, a microplate reader or a biosensor for carrying out fluorescence detection by surface plasmon excitation (SPF). Preferably, label information related to the amount of the measurement target substance can be acquired by fluorescence detection by using surface plasmon resonance.

The configuration of measurement of the fluorescence may be plate reader measurement or flow measurement. In the fluorescence detection method by surface plasmon excitation (SPF method), the measurement can be carried out with higher sensitivity than in a fluorescence detection method by epi-excitation (epi-fluorescence method).

As a surface plasmon fluorescence (SPF) biosensor, a sensor described in JP2008-249361A, comprising: an optical waveguide formed of a material which transmits excitation light of a predetermined wavelength; a metal film formed on one surface of the optical waveguide; a light source for generating a light beam; an optical system for passing the light beam through the optical waveguide and causing the light beam to be incident on an interface between the optical waveguide and the metal film at an incidence angle generating the surface plasmon; and fluorescence detection means for detecting fluorescence generated by being excited by an evanescent wave enhanced due to the surface plasmon can be used.

The fluorescence detection (SPF) system by surface plasmon excitation using the fluorescent particles according to the embodiment of the present invention is preferably an assay method for detecting fluorescence from the fluorescent substance depending on the amount of the measurement target substance immobilized on the metal film on the substrate, and for example, is a method different from a so-called latex agglutination method in which a change in optical transparency by the progress of a reaction in a solution is detected as turbidity. In the latex agglutination method, an antibody-sensitized latex in a latex reagent and an antigen in a biological sample are bound to be agglutinated by an antibody reaction. The latex agglutination method is a method in which the agglutinate increases over time and the antigen concentration is quantified from the change in absorbance per unit time obtained by irradiating the agglutinate with near-infrared light. In the present invention, it is possible to provide a substantially simple method for detecting a measurement target substance, as compared with the latex agglutination method.

(Standardization)

Further, the method according to the embodiment of the present invention may be a method including a labeled particle-related label information acquisition step of acquiring label information related to the amount of the labeled particle; and a standardization step of standardizing label information acquired in a measurement target substance-related label information acquisition step of acquiring label information related to the amount of the measurement target substance, by the label information acquired in the labeled particle-related label information acquisition step.

In a step of bringing a mixed solution containing a biological sample and a luminescently labeled particle having a first binding substance having a binding property to the measurement target substance, and a non-luminescent high molecular particle into contact with a substrate having a detection area (a test area) and a reference area (a control area) to generate the surface plasmon on the detection area and the reference area, and measuring the intensity of emitted fluorescence, a step of measuring the intensity of the fluorescence by the surface plasmon generated on the detection area is the measurement target substance-related label information acquisition step of acquiring label information related to the amount of the measurement target substance, and a step of measuring the intensity of the fluorescence by the surface plasmon generated on the reference area is the labeled particle-related label information acquisition step. A step of acquiring an increase rate in the unit time of the fluorescence intensity acquired in these two steps as change rate of fluorescence signal values and dividing a change rate of signal values of the detection area by a change rate of the signal value of the reference area is a standardization step.

Hereinafter, the present invention will be described in more detail with reference to the Examples of the present invention. The materials, amounts of use, proportions, treatment contents, treatment procedures, and the like shown in the following Examples can be appropriately modified without departing from the spirit and scope of the present invention. Therefore, the scope of the present invention should not be interpreted restrictively by the following specific examples.

EXAMPLES

Explanation of References

Me: methyl group
SDS: sodium dodecyl sulfate
KPS: potassium persulfate
TSH: thyroid stimulating hormone <Method for Measuring Particle Size of Non-Luminescent High Molecular Particle>

4.0 μL of an aqueous dispersion liquid having a solid content of 5% by mass of the non-luminescent high molecular particle was diluted with 796 μL of phosphate saline (PBS, manufactured by FUJIFILM Wako Pure Chemical Corporation) (PH 7.4) and the particle size (hereinafter, referred to as a Z average particle size) and the polydispersion index was measured by using Zetasizer Nano ZS (manufactured by Malvern Panalytical Ltd.).

<Preparation of Non-Luminescent High Molecular Particle>

(Preparation of Non-Luminescent High Molecular Particle 1)

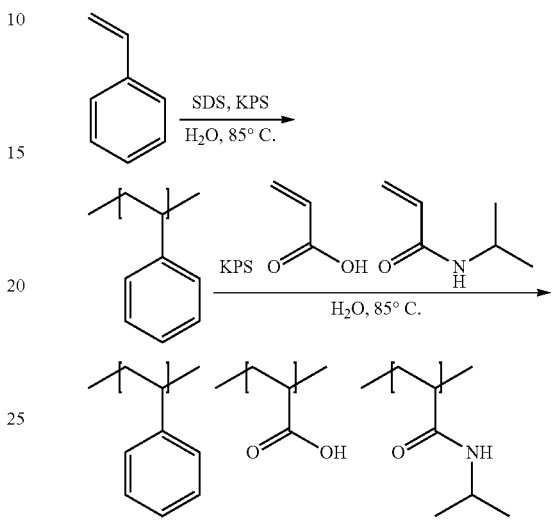

30 g of styrene, 400 g of water, and 2 g of sodium dodecyl sulfate were added to a 1 L flask, and the temperature was raised to 86° C. while stirring at 250 rpm. 30 g of an aqueous solution in which 1 g of potassium persulfate was dissolved was added thereto, and the mixture was stirred at 86° C. for 6 hours. 1.5 g of acrylic acid and 0.375 g of N-isopropyl acrylamide were added thereto, and then 30 g of an aqueous solution in which 1 g of potassium persulfate was dissolved was further added, and the mixture was stirred at 86° C. for 4 hours. After cooling to room temperature, the mixture was filtered through a nylon filter (N-No. 230T), and the obtained aqueous dispersion liquid of fine particles was purified by centrifugation. As a result of the measurement according to the above-described method for measuring a particle size, the Z average particle size of the obtained particles was 47 nm. In addition, it was confirmed that the polydispersion index was less than 0.1 and was monodisperse.

(Preparation of Non-Luminescent High Molecular Particles 2)

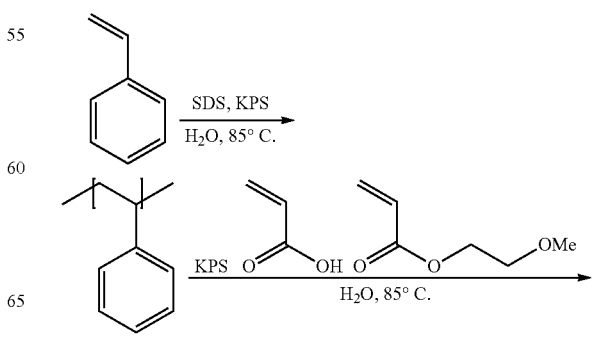

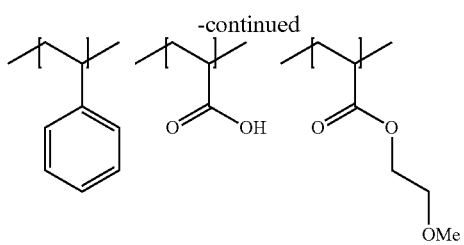

30 g of styrene, 400 g of water, and 2 g of sodium dodecyl sulfate were added to a 1 L flask, and the temperature was raised to 86° C. while stirring at 250 rpm. 30 g of an aqueous solution in which 1 g of potassium persulfate was dissolved was added thereto, and the mixture was stirred at 86° C. for 6 hours. 1.5 g of acrylic acid and 0.375 g of methoxyethyl acrylate were added thereto, and then 30 g of an aqueous solution in which 1 g of potassium persulfate was dissolved was further added, and the mixture was stirred at 86° C. for 4 hours. After cooling to room temperature, the mixture was filtered through a nylon filter (N-No. 230T), and the obtained aqueous dispersion liquid of fine particles was purified by centrifugation. As a result of the measurement according to the above particle size measuring method, the Z average particle size of the obtained particles was 45 nm. In addition, it was confirmed that the polydispersion index was less than 0.1 and was monodisperse.

(Preparation of Non-Luminescent High Molecular Particles 3)

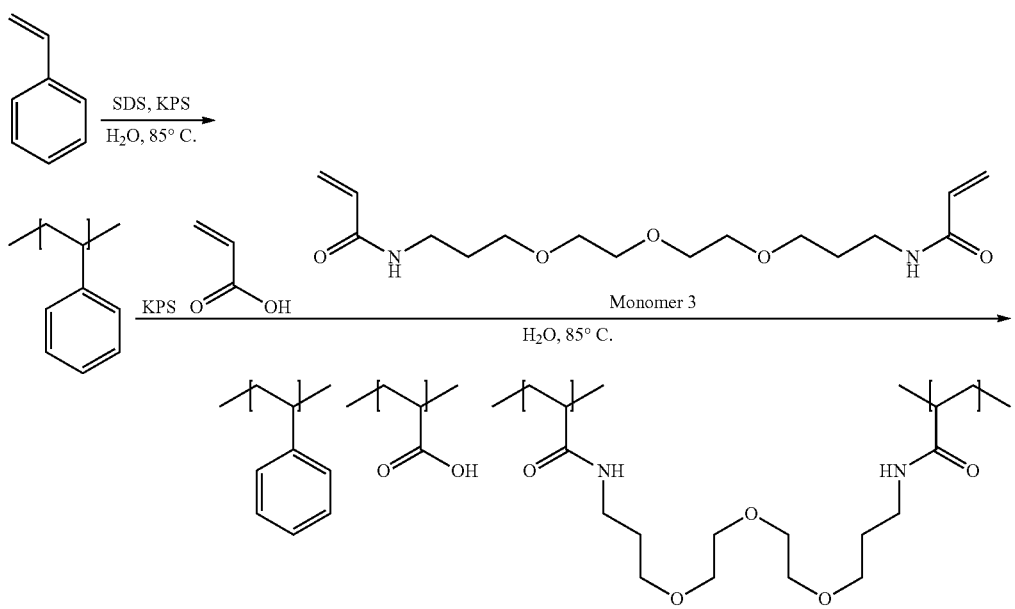

30 g of styrene, 400 g of water, and 2 g of sodium dodecyl sulfate were added to a 1 L flask, and the temperature was raised to 86° C. while stirring at 250 rpm. 30 g of an aqueous solution in which 1 g of potassium persulfate was dissolved was added thereto, and the mixture was stirred at 86° C. for 6 hours. 1.5 g of acrylic acid and 0.375 g of a monomer 3 were added thereto, and then 30 g of an aqueous solution in which 1 g of potassium persulfate was dissolved was further added, and the mixture was stirred at 86° C. for 4 hours. After cooling to room temperature, the mixture was filtered through a nylon filter (N-No. 230T), and the obtained aqueous dispersion liquid of fine particles was purified by centrifugation. As a result of the measurement according to the above-described method for measuring a particle size, the Z average particle size of the obtained particles was 73 nm. The polydispersion index was 0.363.

(Preparation of Particle for Fluorescent Particle)

420 g of ultrapure water was introduced in a 1 L three-neck flask. After raising the temperature to 95° C. in a nitrogen atmosphere, 30 g of styrene was added, and the mixture was stirred for 5 minutes. 1 g of potassium persulfate was dissolved in 30 g of ultrapure water in a separate container, this solution was added in the above-described three-neck flask, and polymerization was carried out at 95° C. for 6 hours. After cooling to room temperature and then filtering through a nylon filter (N-No. 230T), the obtained particles were washed with ultrapure water by centrifugation and purified.

(Preparation of Fluorescent Particle)

7.5 g of an aqueous dispersion liquid having 2% by mass of the above particle solid content and 1.5 mL of tetrahydrofuran were added to a 100 mL eggplant flask, and the mixture was stirred at 30° C. for 20 minutes. In a separate container, 0.9 mg of 3,3',5,5'-tetraphenyl-meso-aza-2,2'-dipyrromethene difluoroborate was dissolved in 0.75 mL of tetrahydrofuran, this mixture was added to the above eggplant flask, and stirring was carried out at 30° C. for 30 minutes. After distilling off tetrahydrofuran under reduced pressure, Kiriyama funnel filtration was carried out, and the particles were washed with PBS (phosphate saline, manufactured by FUJIFILM Wako Pure Chemical Corporation) (pH 7.6) by centrifugation to obtain fluorescent particles.

(Measurement of Particle Size and Polydispersion Index of Fluorescent Particles)

4.0 μL of an aqueous dispersion liquid having a solid content of 2% by mass of the above fluorescent particle solid content was diluted with 796 μL of phosphate saline (PBS, manufactured by FUJIFILM Wako Pure Chemical Corporation) (PH 7.4) and the particle size and the polydispersion index of the fluorescence particles were measured by using Zetasizer Nano ZS (manufactured by Malvern Panalytical Ltd.). The Z average particle size of the obtained particles was 158 nm. In addition, it was confirmed that the polydispersion index was less than 0.1 and was monodisperse.
(Antibody Immobilization)

275 μL of an aqueous dispersion liquid having a solid content of 2% by mass of the above fluorescent particle solid content was diluted with 88 μL of 50 mmol/L MES (2-morpholinoethanesulfonic acid, manufactured by Dojin Chemical Research Institute) buffer solution (pH 5.6) and 8.8 μL of an ultrapure aqueous solution having 10% by mass of 1-ethyl-3-(3-dimethylaminopropyl)carbodiimide hydrochloride (EDC) was added thereto, and then the mixture was stirred at room temperature for 15 minutes. Then, 187 μL of 0.5 mg/mL anti-TSH monoclonal antibody (Anti-TSH Mab MAT04-410, manufactured by Meridian Life Science, Inc.) was added to the mixture and stirred at room temperature for 1 hour to immobilize the antibody on the fluorescent particles. After immobilization, 27.5 μL of an aqueous solution of 2 mol/L glycine was added, and the mixture was allowed to stand for 15 minutes for blocking. After completion of the reaction, purification was carried out by centrifugation to obtain antibody-bound fluorescent particles.

<TSH Evaluation by Sandwich Method>

Using the above fluorescently labeled antibody, thyroid stimulating hormone (TSH) in a biological sample was measured by fluorescence detection by surface plasmon resonance.

A case of quantifying TSH will be described below. The same can also be applied to cases of quantifying substances other than progesterone. First, a biological sample containing TSH and a fluorescently labeled anti-TSH antibody 2 are brought into contact with a TSH immunoassay substrate on which an anti-TSH monoclonal antibody 1 is immobilized. In a case where TSH is present in the biological sample, an antigen-antibody reaction occurs on the substrate between the TSH that has undergone an antigen-antibody reaction with the anti-TSH antibody 2 that has been fluorescently labeled in advance, and the anti-TSH antibody 1 on the substrate. On the other hand, in a case where TSH is not present in the biological sample, an antigen-antibody reaction does not occur between the fluorescently labeled anti-TSH antibody 2 mixed with the biological sample and the anti-TSH antibody 1 on the substrate. After the above reaction is completed, the fluorescently labeled anti-TSH antibody 2 that has not bound to the anti-TSH antibody 1 on the substrate is removed. Next, the degree of formation of an immune complex on the substrate (that is, a complex of the fluorescently labeled anti-TSH antibody 2 and TSH and the anti-TSH antibody 1 on the substrate) is detected as the fluorescence intensity.

(Substrate Preparation)

A polymethyl methacrylate (PMMA) substrate (ACRY-PET (registered trade mark) VH, manufactured by Mitsubishi Chemical Corporation) was prepared, and a gold film having a thickness of 45 nm was prepared on one side by a sputtering method and cut into a width of 7 mm. Seven substrates of the same substrate were prepared. A prepared solution (concentration: 10 μg/mL in 150 mmol/L NaCl solution) containing the-TSH antibody 1 (5409, manufactured by Medix Biochemica) was spotted and dried, whereby a substrate on which the anti-TSH antibody was immobilized. The prepared substrate was washed by repeating three times of wash with 300 μL of a PBS solution (pH 7.4) prepared in advance, containing 0.05% by mass of Tween 20 (polyoxyethylene (20) sorbitan monolaurate, FUJIFILM Wako Pure Chemical Corporation). After completion of the washing, in order to block an anti-TSH antibody-unadsorbed portion on the gold film, 300 μL of a PBS solution (pH 7.4) containing 1% by mass of casein (manufactured by Thermo Fisher Scientific Inc.) was added, followed by being left to stand for 1 hour at room temperature. After washing with the washing solution, 300 μL of Immunoassay Stabilizer (manufactured by Advanced Biotechnologies Inc.) was added as a stabilizer thereto and left to stand for 30 minutes at room temperature, and then the solution was removed completely, whereby a substrate for evaluation was prepared.

(Preparation of Sensor Chip)

Figure 2:
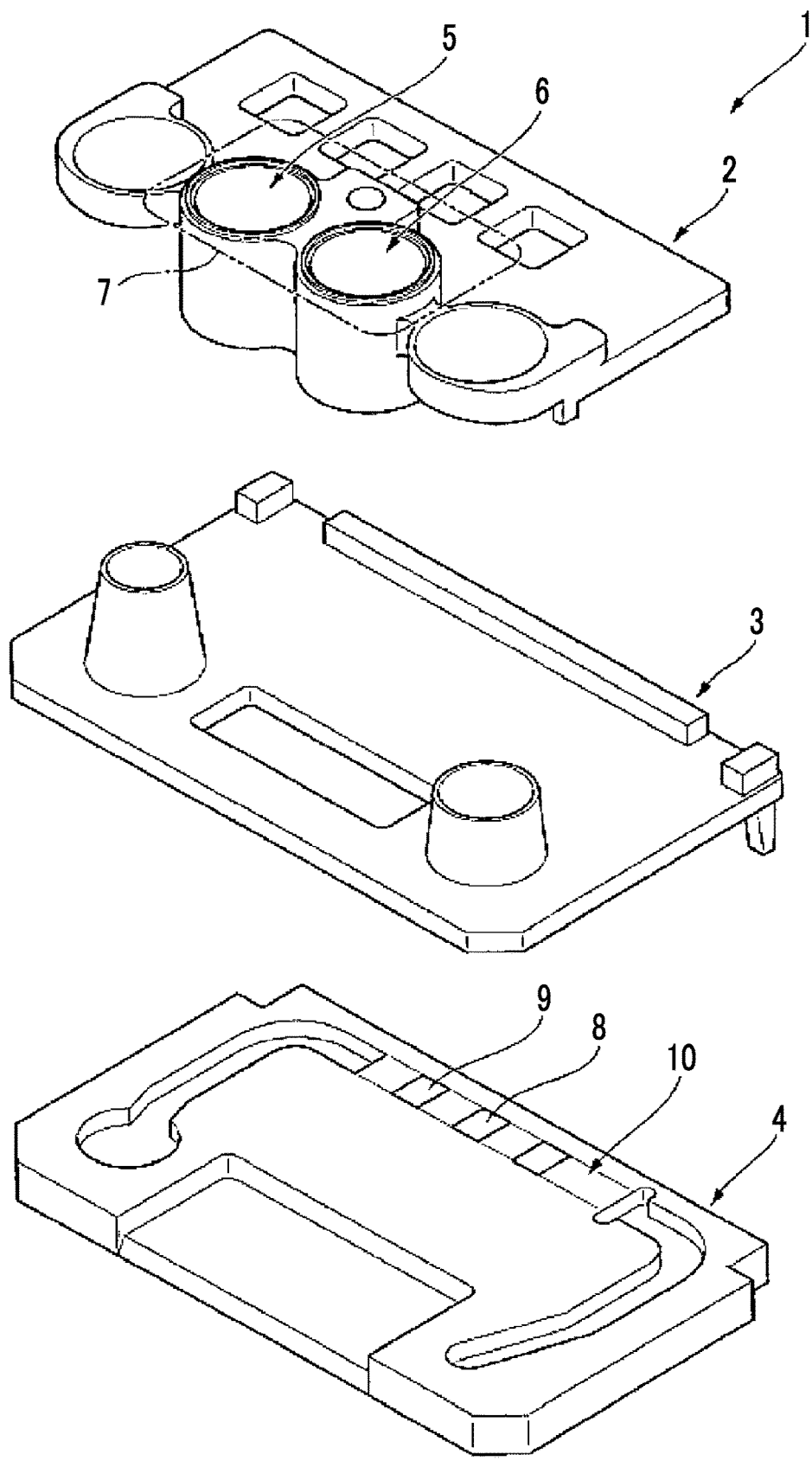
FIG. 2 is an exploded view illustrating the sensor chip.

A flow channel-type sensor chip was prepared to have the configuration of the second embodiment in JP2010-190880A. The schematic views thereof are shown in FIG. 1 and FIG. 2. FIG. 1 is a schematic view of a sensor chip 1, and FIG. 2 is an exploded view of the sensor chip 1. The sensor chip 1 includes an upper member 2, an intermediate member 3, and a substrate 4. The upper member 2 is provided with a first container 5 and a second container 6. The first container 5 and the second container 6 are collectively referred to as a container group 7. A flow channel 10 is formed in the substrate 4, and a detection area 8 and a reference area 9 are formed on the flow channel 10.

(Preparation of Test Sample)

As test samples, dog sera having TSH concentrations of about 0 ng/mL and about 0.4 ng/mL were used. As the dog serum, a serum of an oriental beagle dog purchased from KITAYAMA LABES Co., Ltd. was prepared.

(TSH Evaluation)

Using the fluorescently labeled antibody prepared above, TSH measurement carried out with IMMUNO AU10V (manufactured by FUJIFILM Corporation). A mixed solution of 100 μL of the test sample (the dog serum) prepared above and a fluorescently labeled anti-TSH antibody (0.04 mg in terms of the weight of the fluorescent particles) was prepared, an aqueous dispersion liquid of the non-luminescent polymer described in the table below was added (in Example 1, 10 μL of an aqueous dispersion liquid having 12% by mass of a solid content of the non-luminescent high molecular particles 1 was added, that is, 1.2 mg in terms of the solid content was added) to the mixed solution, and the resultant mixture was stirred for 10 minutes. Next, each mixed solution of the fluorescently labeled antibody and the test sample was spotted on a flow channel type sensor chip in which the substrate prepared above was enclosed. After spotting, the mixed solution was allowed to flow down at a rate of 10 μL/min while aspirating with a pump to bring the mixed solution into contact with the gold film surface on which the anti-TSH antibody had been immobilized, and then the fluorescence intensity was continuously measured for 1.5 minutes. The rate of increase in the fluorescence intensity obtained on the substrate in a unit time was determined. The S/N was determined from the increase rate of the obtained two test samples, and the relative S/N was compared. A calculation expression used for the evaluation standards is shown below.

S/N=(increase rate obtained from test sample having TSH concentration of about 0.4 ng/mL)/(increase rate obtained from test sample having TSH concentration of about 0 ng/mL)

Relative S/N=(S/N of each of Examples and Comparative Examples)/(S/N of Comparative Example 1)

(Relative S/N)
S: 2.0 or more
A: 1.7 or more and less than 2.0
B: 1.4 or more and less than 1.7
C: 1.1 or more and less than 1.4
D: less than 1.1

TABLE 1

| | Non-luminescent high molecular particle | Other additives | Addition amount of non-luminescent high molecular particle or other additives | Addition method of non-luminescent high molecular particle or other additives | Weight ratio to fluorescent particle | Relative S/N evaluation |
|---|---|---|---|---|---|---|
| Example 1 | Particle 1 | Absent | 1.2 mg | Addition of 10 μL of aqueous dispersion liquid having solid content of 12% by mass | 30 times | S |
| Example 2 | Particle 2 | Absent | 1.2 mg | Addition of 10 μL of aqueous dispersion liquid having solid content of 12% by mass | 30 times | A |
| Example 3 | Particle 2 | Absent | 0.5 mg | Addition of 10 μL of aqueous dispersion liquid having solid content of 5% by mass | 12.5 times | B |
| Example 4 | Particle 3 | Absent | 1.2 mg | Addition of 10 μL of aqueous dispersion liquid having solid content of 12% by mass | 30 times | A |
| Comparative Example 1 | Absent | Absent | Absent | Absent | Absent | D *3 |
| Comparative Example 2 | Absent | (Water-soluble) polyacrylic acid | 0.5 mg | Addition of 10 μL of aqueous dispersion liquid having solid content of 5% by mass | 12.5 times | Unevaluable *1 |
| Comparative Example 3 | Absent | (Water-soluble) polyacrylic acid | 0.05 mg | Addition of 10 μL of aqueous dispersion liquid having solid content of 0.5% by mass | 1.25 times | D |
| Comparative Example 4 | Absent | (Water-soluble) polyacrylamide | 0.5 mg | Addition of 10 μL of aqueous dispersion liquid having solid content of 5% by mass | 12.5 times | Unevaluable *2 |
| Comparative Example 5 | Absent | (Water-soluble) polyacrylamide | 0.05 mg | Addition of 10 μL of aqueous dispersion liquid having solid content of 0.5% by mass | 1.25 times | D |
| Comparative Example 6 | Absent | Hydrophilic silica particle | 0.5 mg | Addition of 10 μL of aqueous dispersion liquid having solid content of 5% by mass | 12.5 times | Unevaluable *1 |

Unevaluable *1: Serum gelation occurred, and evaluation by the sandwich method was not possible due to deterioration of fluidity.

Unevaluable *2: Fluorescent particles were non-specifically adsorbed on the gold substrate, and even in a serum sample with a TSH concentration of about 0 ng/mL, the fluorescence intensity exceeded the quantification limit, and thus the amount of TSH could not be evaluated.

*3: Since the relative S/N is defined by the relative ratio to the S/N of Comparative Example 1, the relative S/N of Comparative Example 1=1.

In a case where the relative S/N evaluation of S, A, and B is defined as acceptable, and the relative S/N evaluation of C and D is defined as unacceptable, all the non-luminescent high molecular particles according to the embodiment of the present invention were acceptable. In Examples of the present invention, it can be seen that the antibody binding amount and the non-specific adsorption inhibitory effect can be compatible with each other, and the test sample can be detected with high sensitivity. As shown in Comparative Examples 2, 4, and 6, in the case of additives (a water-soluble polymer and an inorganic fine particle) other than those used in the present invention, the evaluation was impossible due to deterioration of fluidity or non-specific adsorption. In Comparative Examples 3 and 5 in which the addition amount was reduced, the relative S/N was unacceptable.

In Comparative Examples, the following additives were added.

(Water-soluble) polyacrylic acid: manufactured by FUJIFILM Wako Pure Chemical Corporation, average molecular weight: about 25,000

(Water-soluble) polyacrylamide: manufactured by Sigma-Aldrich Co., LLC, average molecular weight: about 40,000
Hydrophilic silica particles: manufactured by NIPPON AEROSIL Co., Ltd., hydrophilic fumed silica specific surface area: 130 m$^2$/g

EXPLANATION OF REFERENCES

1: sensor chip
2: upper member
3: intermediate member
4: substrate
5: first container
6: second container
7: container group
8: detection area
9: reference area
10: flow channel

What is claimed is:
1. A kit for measuring a measurement target substance in a biological sample, the kit comprising:
   a luminescently labeled particle that has a first binding substance having a binding property to a measurement target substance;
   a substrate that has a detection area on a metal film having a second binding substance having a binding property to any one of the measurement target substance or the first binding substance; and a non-luminescent high molecular particle that contains a structural unit represented by Formula (A) or Formula (B),

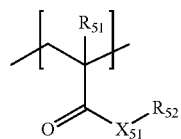

in the formula, $R_{51}$ represents a hydrogen atom or a methyl group, $X_{51}$ represents an oxygen atom or $NR_{53}$, and $R_{52}$ represents a substituted or unsubstituted alkyl group, a substituted or unsubstituted aryl group, or a substituted or unsubstituted heteroaryl group, where $R_{53}$ represents a hydrogen atom, a substituted or unsubstituted alkyl group, a substituted or unsubstituted aryl group, or a substituted or unsubstituted heteroaryl group, and

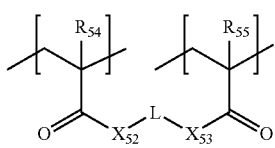

in the formula, $R_{54}$ and $R_{55}$ each independently represent a hydrogen atom or a methyl group, $X_{52}$ and $X_{53}$ each independently represent an oxygen atom or $NR_{56}$, and L represents a substituted or unsubstituted polyalkyleneoxy chain, a substituted or unsubstituted alkylene group, a substituted or unsubstituted arylene group, or a substituted or unsubstituted heteroarylene group, where $R_{56}$ represents a hydrogen atom, a substituted or unsubstituted alkyl group, a substituted or unsubstituted aryl group, or a substituted or unsubstituted heteroaryl group, wherein the luminescently labeled particle is a particle that contains a fluorescent dye represented by Formula (1) or a fluorescent dye represented by Formula (10),

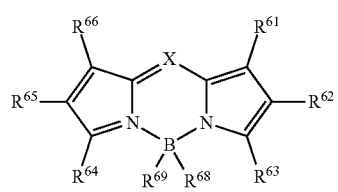

in the formula, X represents $CR^{67}$ or N, $R^{61}$ to $R^{67}$ represents a hydrogen atom, an alkyl group, a cycloalkyl group, an aliphatic heterocyclic group, an alkenyl group, a cycloalkenyl group, an alkynyl group, a hydroxyl group, a mercapto group, an alkoxy group, an alkylthio group, an aryloxy group, an arylthio group, an aryl group, a heteroaryl group, a halogen atom, a cyano group, a formyl group, an R—CO-group, a carboxy group, an R—O—CO-group, an R—CO—O-group, an $(R^A)_2$N—CO-group, an amino group, a nitro group, or a silyl group, which may further have a substituent, where R represents an alkyl group, a cycloalkyl group, an aliphatic heterocyclic group, an alkenyl group, a cycloalkenyl group, an alkynyl group, an aryl group, or a heteroaryl group, and $R^A$ represents a hydrogen atom, an alkyl group, a cycloalkyl group, an aliphatic heterocyclic group, an alkenyl group, a cycloalkenyl group, an alkynyl group, an aryl group, or a heteroaryl group, and $R^{68}$ and $R^{69}$ represent an alkyl group, a cycloalkyl group, an aliphatic heterocyclic group, an alkenyl group, a cycloalkenyl group, an alkynyl group, a hydroxyl group, a mercapto group, an alkoxy group, an alkylthio group, an aryloxy group, an arylthio group, an aryl group, a heteroaryl group, or a halogen atom, which may further have a substituent, and

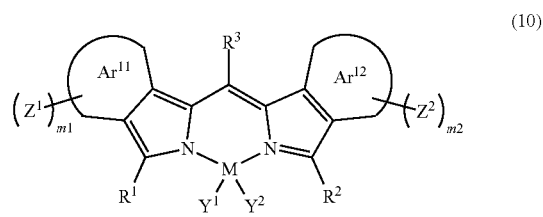

in the formula, m1 and m2 each independently represent an integer of 0 to 4, and any one of m1 or m2 is at least one, M represents a metalloid atom or a metal atom, $R^1$, $R^2$, and $R^3$ each independently represent a hydrogen atom, an alkyl group, an aryl group, a heterocyclic group, an ethenyl group, an ethynyl group, an acyl group, an alkoxy group, an aryloxy group, an alkylthio group, or an arylthio group, which may have a substituent, $Y^1$ and $Y^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, which may have a substituent, and $Y^1$ and $Y^2$ may be linked to each other to form a ring, $Ar^{11}$ and $Ar^{12}$ each independently represent an aromatic ring which may have a substituent, $Z^1$ and $Z^2$ each independently represent an aryl group, a heterocyclic group, or an amino group, which may have a substituent, and in a case where m1 is two or more, a plurality of $Z^1$'s may be the same group or groups different from each other, and in a case where m2 is two or more, a plurality of $Z^2$'s may be the same group or groups different from each other, wherein the non-luminescent high molecular particle is a latex obtained by homogeneously suspending a synthetic polymer, wherein the non-luminescent high molecular particle contains a styrene unit, a unit of acrylic acid or a salt thereof, or a unit of methacrylic acid or a salt thereof, as a structural unit other than the structural unit represented by Formula (A) or Formula (B), and a core particle of the non-luminescent high molecular particle consists of a homopolymer of styrene, and the structural unit represented by Formula (A) or Formula (B) is present on the surface of the particles.

2. The kit according to claim 1, wherein the luminescently labeled particles have an average particle size of 50 to 300 nm.

3. The kit according to claim 1,
wherein the non-luminescent high molecular particles have an average particle size of 10 to 300 nm.

4. The kit according to claim 1,
wherein a polydispersion index of the non-luminescent high molecular particle is 0.40 or less.

5. A method for measuring a measurement target substance in a biological sample, the method comprising:
a capturing step of bringing a mixture of a biological sample, a luminescently labeled particle that has a first binding substance having a binding property to a measurement target substance, and a non-luminescent high molecular particle that contains a structural unit represented by Formula (A) or Formula (B) into contact with a substrate that has a detection area on a metal film having a second binding substance having a binding property to any one of the measurement target substance or the first binding substance, thereby capturing the luminescently labeled particle on the substrate;
a label information acquisition step for acquiring label information related to the measurement target substance,

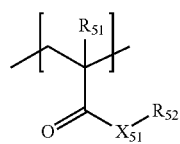
(A)

in the formula, $R_{51}$ represents a hydrogen atom or a methyl group, $X_{51}$ represents an oxygen atom or $NR_{53}$, $R_{52}$ represents a substituted or unsubstituted alkyl group, a substituted or unsubstituted aryl group, or a substituted or unsubstituted heteroaryl group, where $R_{53}$ represents a hydrogen atom, a substituted or unsubstituted alkyl group, a substituted or unsubstituted aryl group, or a substituted or unsubstituted heteroaryl group, and

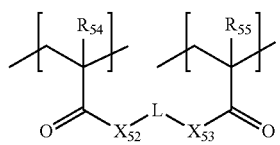
(B)

$R_{54}$ and $R_{55}$ each independently represent a hydrogen atom or a methyl group, $X_{52}$ and $X_{53}$ each independently represent an oxygen atom or $NR_{56}$, and L represents a substituted or unsubstituted polyalkyleneoxy chain, a substituted or unsubstituted alkylene group, a substituted or unsubstituted arylene group, or a substituted or unsubstituted heteroarylene group, where $R_{56}$ represents a hydrogen atom, a substituted or unsubstituted alkyl group, a substituted or unsubstituted aryl group, or a substituted or unsubstituted heteroaryl group; and
a measurement step for acquiring label information related to the measurement target substance and measuring for the measurement target substance,
wherein the luminescently labeled particle is a particle that contains a fluorescent dye represented by Formula (1) or a fluorescent dye represented by Formula (10),

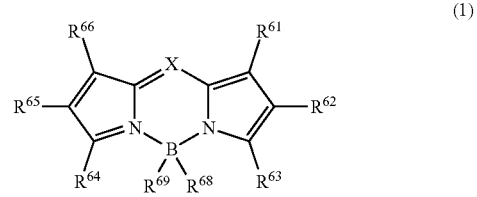
(1)

in the formula, X represents $CR^{67}$ or N,
$R^{61}$ to $R^{67}$ represents a hydrogen atom, an alkyl group, a cycloalkyl group, an aliphatic heterocyclic group, an alkenyl group, a cycloalkenyl group, an alkynyl group, a hydroxyl group, a mercapto group, an alkoxy group, an alkylthio group, an aryloxy group, an arylthio group, an aryl group, a heteroaryl group, a halogen atom, a cyano group, a formyl group, an R—CO-group, a carboxy group, an R—O—CO-group, an R—CO—O-group, an $(R^A)_2$N-CO-group, an amino group, a nitro group, or a silyl group, which may further have a substituent,
where R represents an alkyl group, a cycloalkyl group, an aliphatic heterocyclic group, an alkenyl group, a cycloalkenyl group, an alkynyl group, an aryl group, or a heteroaryl group, and $R^A$ represents a hydrogen atom, an alkyl group, a cycloalkyl group, an aliphatic heterocyclic group, an alkenyl group, a cycloalkenyl group, an alkynyl group, an aryl group, or a heteroaryl group, and
$R^{68}$ and $R^{69}$ represent an alkyl group, a cycloalkyl group, an aliphatic heterocyclic group, an alkenyl group, a cycloalkenyl group, an alkynyl group, a hydroxyl group, a mercapto group, an alkoxy group, an alkylthio group, an aryloxy group, an arylthio group, an aryl group, a heteroaryl group, or a halogen atom, which may further have a substituent, and

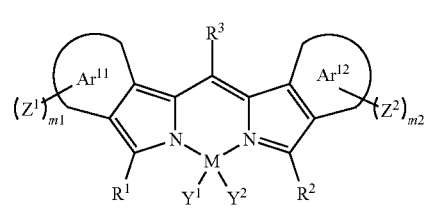
(10)

in the formula, m1 and m2 each independently represent an integer of 0 to 4, and any one of m1 or m2 is at least one, M represents a metalloid atom or a metal atom, $R^1$, $R^2$, and $R^3$ each independently represent a hydrogen atom, an alkyl group, an aryl group, a heterocyclic group, an ethenyl group, an ethynyl group, an acyl group, an alkoxy group, an aryloxy group, an alkylthio group, or an arylthio group, which may have a substituent, $Y^1$ and $Y^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, which may have a substituent, and $Y^1$ and $Y^2$ may be linked to each other to form a ring, $Ar^{11}$ and $Ar^{12}$ each independently represent an aromatic ring which may have a substituent, $Z^1$ and $Z^2$ each independently represent an aryl group, a heterocyclic group, or an amino group, which may have a substituent, and in a case where m1 is two or more, a plurality of $Z^1$'s may be the same group or groups different from each other, and in a case where m2 is two or more, a plurality of $Z^2$'s may be the same group or groups different from each other, Wherein the non-luminescent high molecular particle is a latex obtained by homogeneously suspending a synthetic polymer, wherein the non-luminescent high molecular particle contains a styrene unit, a unit of acrylic acid or a salt thereof, or a unit of methacrylic acid or a salt thereof, as a structural unit other than the structural unit represented by Formula (A) or Formula (B), and a core particle of the non-luminescent high molecular particle consists of a homopolymer of styrene, and the structural unit represented by Formula (A) or Formula (B) is present on the surface of the particles.

6. The method according to claim 5, wherein an amount of the non-luminescent high molecular particle used is 1 to 1000 times an amount of the luminescently labeled particle.

\* \* \* \* \*